United States Patent [19]

Mhatre et al.

[11] Patent Number: 5,326,372
[45] Date of Patent: Jul. 5, 1994

[54] PROSTHETIC HEART VALVE ASSEMBLY

[75] Inventors: Harischandra K. Mhatre, Mahim Bombay; Bhagavant R. Kalke, Worli, both of India

[73] Assignee: Kalke Mhatre Associates, Bombay, India

[21] Appl. No.: 951,805

[22] Filed: Sep. 28, 1992

[30] Foreign Application Priority Data

Mar. 26, 1992 [IN] India .............. 92/BOM/92

[51] Int. Cl.⁵ .................. F16K 15/00; A61F 2/24
[52] U.S. Cl. ........................... 623/2; 137/527
[58] Field of Search ............. 623/2, 1; 137/531, 527

[56] References Cited

U.S. PATENT DOCUMENTS

| Re. 31,040 | 3/1978 | Possis. | |
|---|---|---|---|
| 4,276,658 | 7/1981 | Hanson | 623/2 |
| 4,308,624 | 1/1982 | Klawitter. | |
| 4,326,304 | 4/1982 | Klawitter. | |
| 4,328,592 | 5/1982 | Klawitter. | |
| 4,357,715 | 11/1982 | Klawitter. | |
| 4,416,029 | 11/1983 | Kaster. | |
| 4,451,937 | 6/1984 | Klawitter | 623/2 |
| 4,689,046 | 8/1987 | Bokros | 623/2 |
| 4,731,075 | 3/1988 | Gallo Mezo et al. | |
| 4,808,180 | 2/1989 | Johnson. | |
| 4,863,458 | 9/1989 | Bokros. | |
| 4,863,467 | 9/1989 | Bokros. | |
| 4,888,010 | 12/1989 | Bokros. | |
| 4,935,030 | 6/1990 | Alonso | 623/2 |
| 5,061,278 | 10/1991 | Bicer | 623/2 |
| 5,078,738 | 1/1992 | Couetil | 623/2 |
| 5,152,785 | 10/1992 | Bokros et al. | 623/2 |

OTHER PUBLICATIONS

Brochure by SKF on "Spherical Plain Bearings" and Self-Aligning Ball Bearings.

Primary Examiner—Randall L. Green
Assistant Examiner—Dinh X. Nguyen
Attorney, Agent, or Firm—C. C. Shroff

[57] ABSTRACT

A prosthetic heart valve assembly of the type having a ring member and pivotable leaflet structure is provided. Each individual leaflet pivots on a pair of peripheral flat ear members that oscillate in mating respective spherical bearing recesses. These recesses are formed in separate bearing blocks that radially seatingly engage midwall holes in a rigid, cross-sectionally C-configured ring member. Retaining means holds the bearing blocks in association with the ring member. Edge portions of the ear members and adjacent leaflet edges wipe the recesses and adjacent bearing block surfaces, thereby to avoid blood stagnation and clotting.

23 Claims, 12 Drawing Sheets

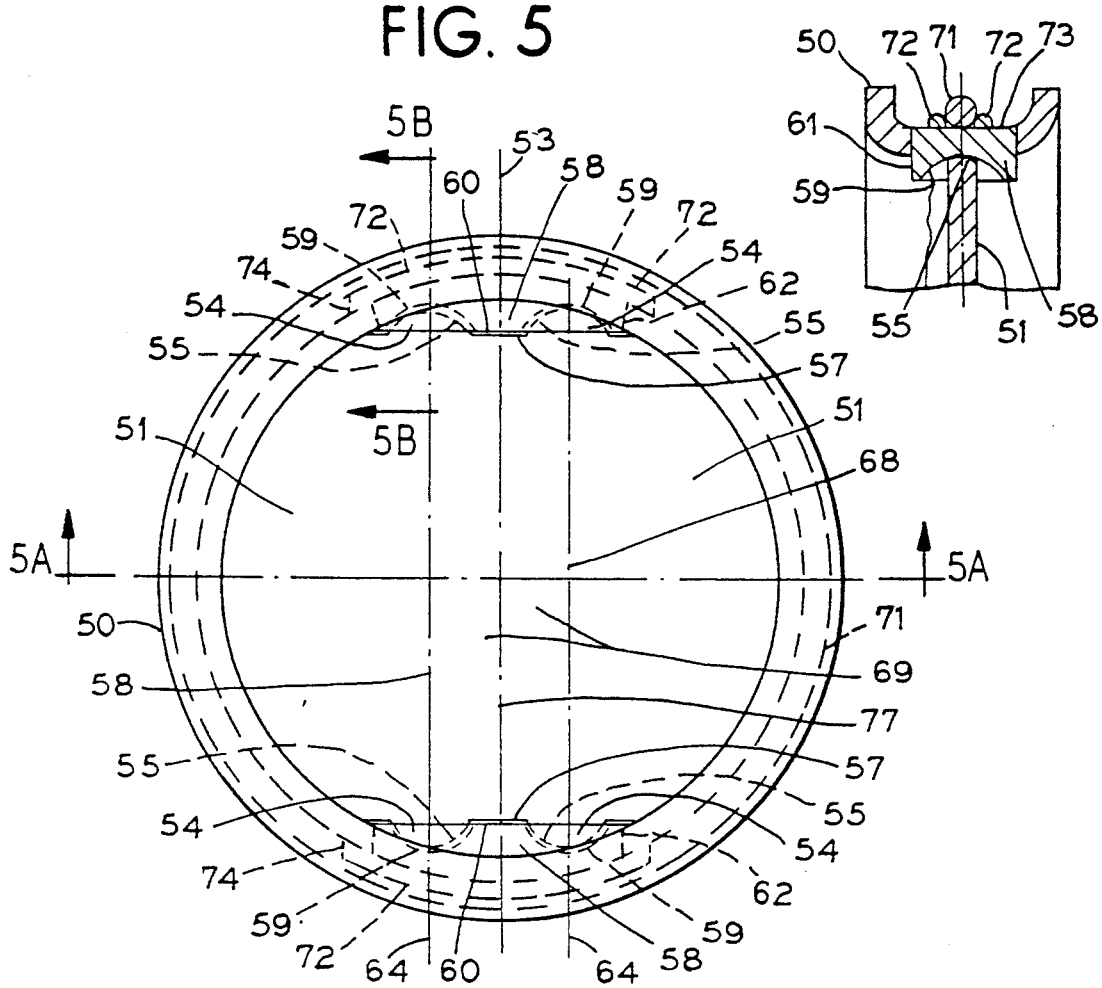

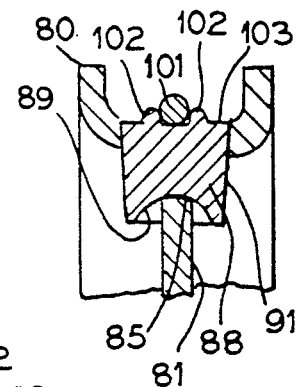
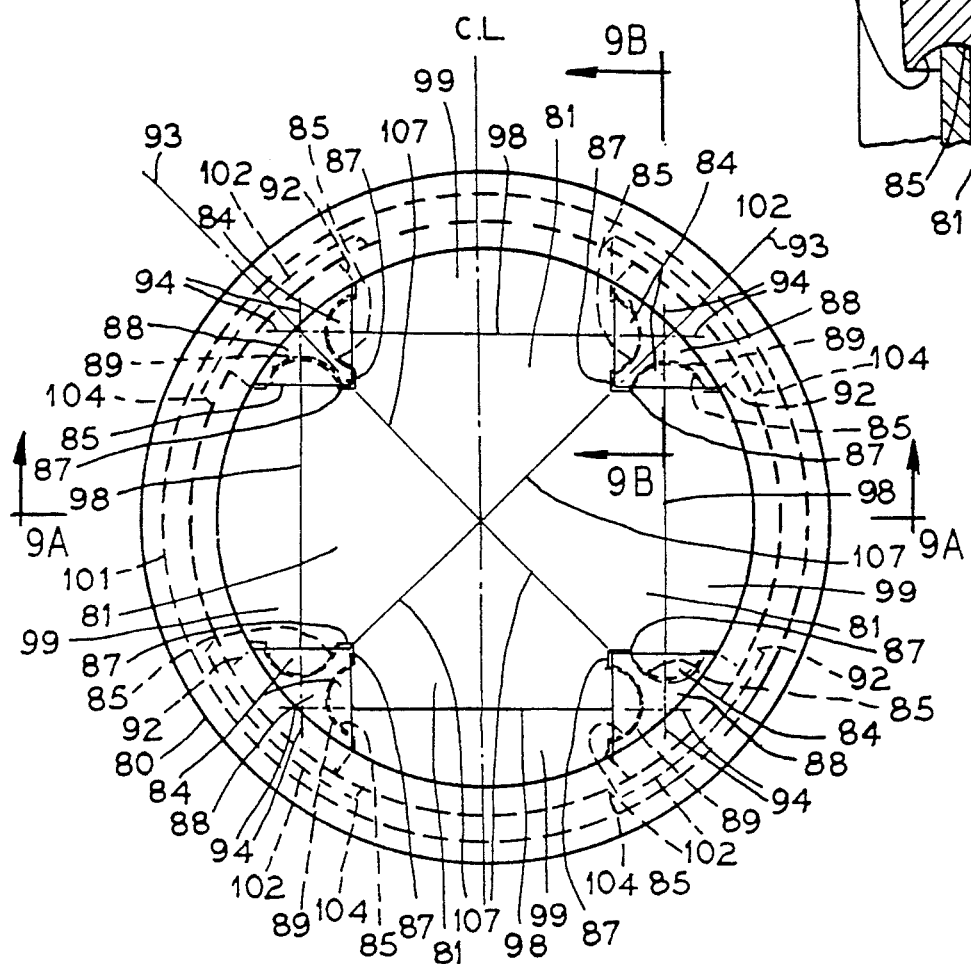
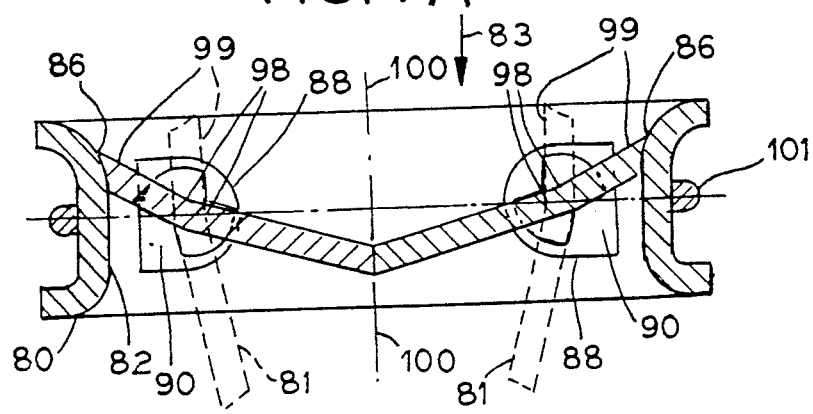

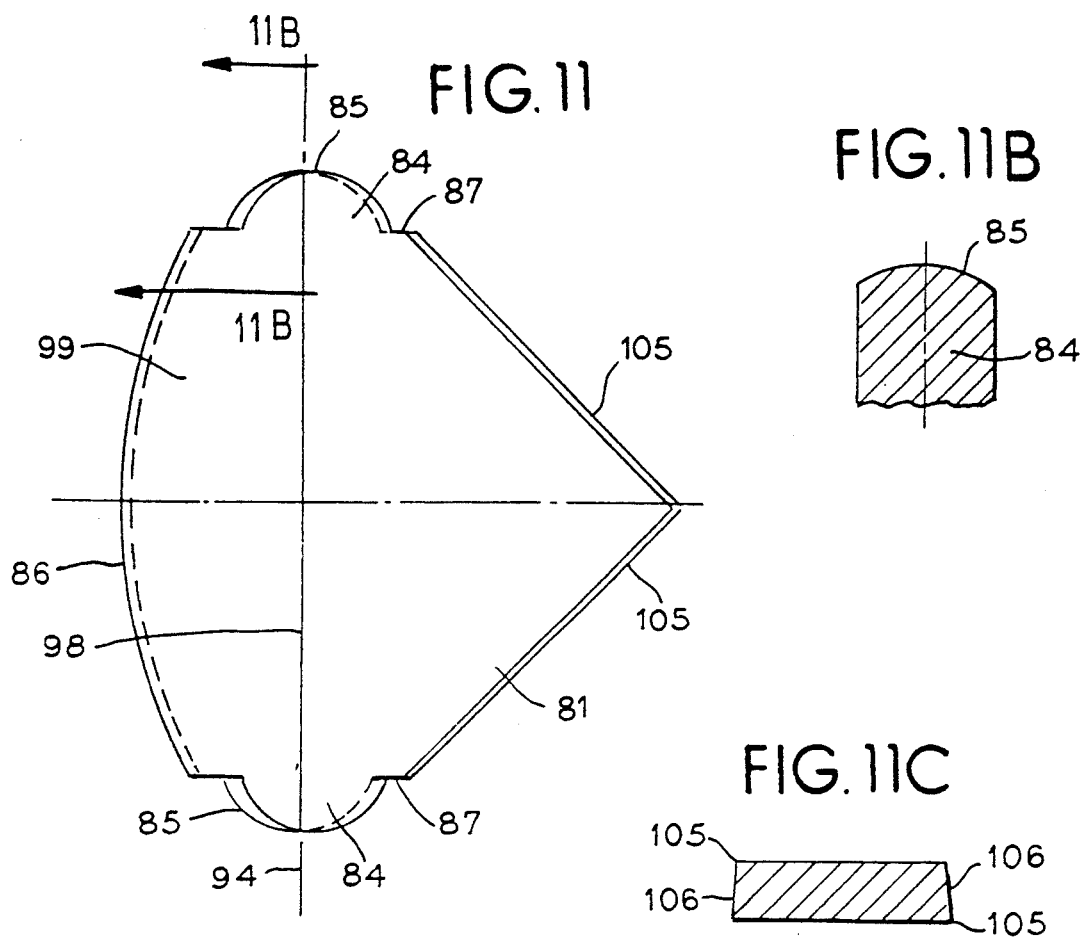
FIG. 11
FIG. 11B
FIG. 11C
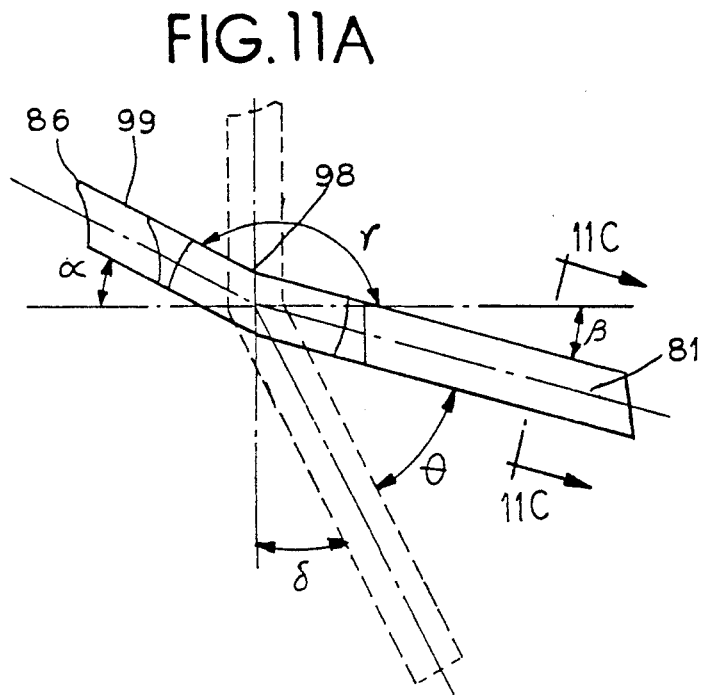
FIG. 11A

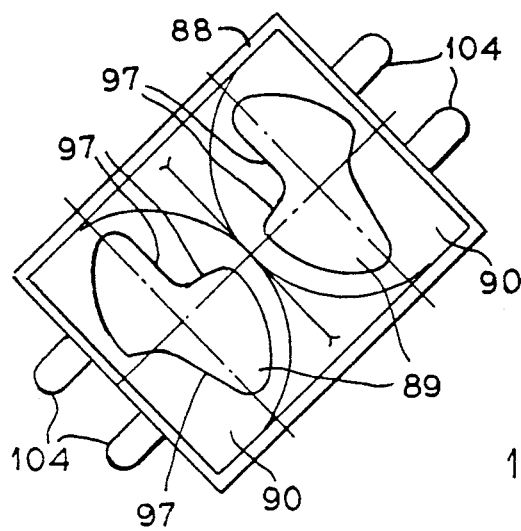
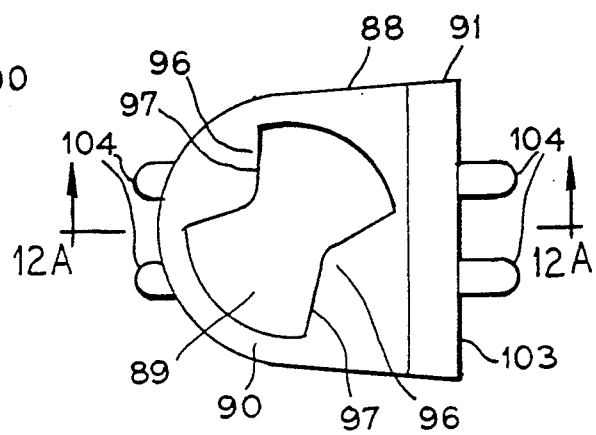
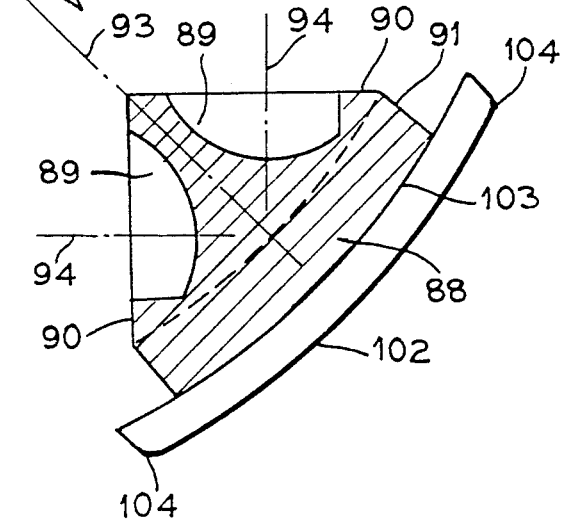
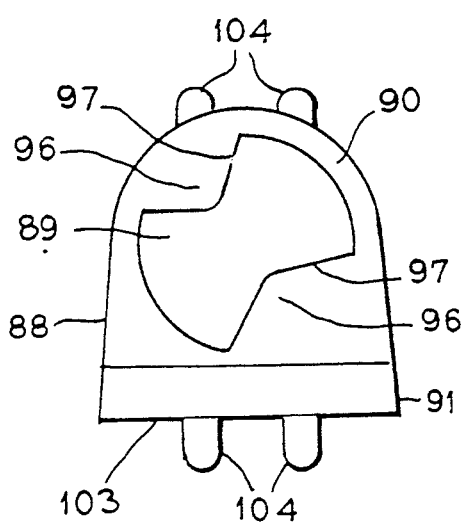

PROSTHETIC HEART VALVE ASSEMBLY

FIELD OF THE INVENTION

This invention relates to improvements in prosthetic heart valves.

BACKGROUND OF THE INVENTION

The basic function of a prosthetic heart valve is to provide a unidirectional blood flow valve in a mammalian (especially human) cardiac system to achieve efficient single direction blood circulation in the circulatory system when the valve is surgically implanted to replace a damaged or defective heart valve.

Typically, a prosthetic heart valve assembly, particularly one intended for human use, comprises a main valve body that comprises an annular ring member which is generally provided with skirt means to aid in surgically securing the ring member to a patient's cardiac system in a desired position. The ring member includes a generally centrally located passageway for flow therethrough of blood, and the passageway is provided with valve flow controlling means to achieve unidirectional flow of blood through the passageway. A valve flow controlling means can utilize a moveable ball or flap (in a form of a disc or leaflet) and includes guidance means that holds same in operative association with the ring member and that also allows same to move between open and closed positions. Examples of guidance means include a cage, projections from the ring member, recesses on the inner wall of the ring member with matching projections provided on the flow controlling means, and the like.

The efficacy of a heart valve prosthesis depends mainly on the blood flow regulating means, including its profile and its guidance means. In a particular design of a heart valve prosthesis, the construction materials used for its structure, design and fabrication, and its profile and localized wear characteristics, contribute to the prosthesis service capability and long-term operational reliability. Heart valve prosthesis failure can occur as a result of stagnation of blood leading to undesirable clot formation, tissue growth, excessive leakage of blood through or around the prosthesis, or other malfunction or disruption.

In a ball and cage type of heart valve prosthesis, the ball is made of synthetic polymeric material or of metal and is retained in a cage during its movements from open to closed positions (inclusive) to control unidirectional flow of the blood through the ring member which is made of metal. The disadvantages of such a prosthesis are mainly that the cage is fixed on the ring member and projects out from the ring member excessively into the heart chamber or the main artery, while the ball totally prevents desired central blood flow through the ring member when the valve is in its open position.

In a single disc (or single leaflet) prior art type of heart valve prosthesis, the disc is made either of material coated with pyrolytic carbon or synthetic polymeric materials, and the disc is mounted to move from open to closed positions (inclusive) either by projecting struts (or ears) or within a cage fixed on the ring member and usually made of metal. A disc having a flat or a curved surface does create some resistance to central flow of blood through the ring member when the disc is in its open position. As all portions of the struts or cage of a single disc prosthetic heart valve, as well as all portions of the ball and cage type prosthetic heart valve, are not wiped off equally or regularly, localized blood clots tend to form resulting in growth of tissues on them in due course. These tissues prevent free movement of the disc or the ball and prevent smooth flow of blood through the ring member particularly at later stages. These tissues also occasionally detach and produce embolisms. If wires associated with the cage or the pivoting means are welded to the ring member, there is potential danger of weld fracture and component separation at the welded joints.

Bi-leaflet (or double leaflet) prior art types of heart valve prostheses each have a ring member and two semi-circularly shaped leaflets to control unidirectional flow of blood through the ring member. The ring member and both the leaflets are preferably made of a material coated with pyrolytic carbon. Each leaflet has an outer peripheral circular edge that joins radial straight edge portions to form a semi-circularly shaped body. Each leaflet has a pair of opposed ears situated at locations on its circular edge adjacent to the ends of the straight edge portions. The ears are adapted to engage recesses provided on the inner wall of the ring member to form a hinge-like bearing structure. The two leaflets oscillate independently about their respective hinge axes and each leaflet in its closed position covers about one half of the passageway through the ring member. The two hinged leaflets as conventionally mounted across the passageway create some resistance to central flow of blood through the passageway when the leaflets are in their open positions. The ring member is unitarily constructed to incorporate the recesses for the ears.

An assembly process for such a prior art heart valve prosthesis involves engaging the leaflet ears with the ring member recesses, and that assembly process must be accomplished by deforming the pyrolytic carbon coated ring member. A coating of pyrolytic carbon material is rigid or less flexible than the underlying material so that the engagement of the ears into the recesses must involve a minimum of flexing and a bare minimum bearing surface of engagement after flexing. A little more flexing is achieved either by providing two arm projections (preferably flat) for the recesses on either the inlet or the outlet side of the ring member, or, alternatively, by making the ring member thin in its cross-section so as to make it slightly more flexible. However, the possibilities of residual permanent deformation of the ring member, or of cracking of the ring member, in the assembly process cannot be completely eliminated, and the resulting minimum bearing engagement makes the ears of each leaflet prone to slipping or dislodgement from their recesses when the resulting prosthesis is in use.

The flat arm projections on the ring member make it very cumbersome and require extra efforts to insert the resulting heart valve prosthesis into an appropriate position in the patient's heart body, particularly during an aortic valve replacement operation. The alternative of a thin cross-section for the ring member hardly provides the minimum required rigidity for a ring member making the resulting heart valve prosthesis intrinsically a weak device. The unitary construction of the ring member with its recesses to accommodate the ears of the leaflets results in an inherent inability to adjust axial end-play precisely in the hinging mechanism such as is necessary to minimize malfunction, disruption and ultimate dislodgement of the leaflets over a period of time in use.

Thus, provision of either flat arm projections on the ring member, or a thin cross-section in the ring member, together with the minimum bearing surface engagement between the ears and the recesses, plus the inability to adjust axial end-play in the hinging mechanism, limits long-term reliable service of the presently available bi-leaflet heart valve prostheses.

Since safety of human life is involved, to achieve efficient and reliable service of heart valve prostheses, improved structures and fabrication processes are needed. Even a very small failure rate for a heart valve prosthesis is undesirable. There is a need for a new and improved heart valve prosthesis of the leaflet type which surpasses the performance and the reliability of presently available prior art heart valve prostheses. Moreover, an improved heart valve prosthesis should achieve optimal expected long service life characteristics. The present invention provides such an improved type of heart valve prosthesis.

SUMMARY OF THE INVENTION

More particularly, this invention relates to a class of new and improved prosthetic heart valve assemblies.

Such an assembly is adapted to provide very reliable and efficient service when surgically implanted particularly in a human heart and also to have a useful and trouble free life of at least several years, thereby to outlast the actual typical average lifespan of the human being in whose heart such a valve assembly has been so implanted.

The inventive heart valve prosthesis utilizes a leaflet-type valve flow controlling means (or flap structure) that has either a single or a multiple (including double) leaflet disposition and that has new and improved structural characteristics. The valve flow controlling means is located generally within and across the central passageway of the ring member of an annular valve body structure having new and improved structural characteristics. The valve flow controlling means is pivotable in response to fluidic pressure variations applied on the upstream side thereof and achieves one way fluid flow through the passageway.

A single leaflet valve means, when used, has circular outer peripheral edge portions which in the leaflet closed position are adapted to meet and sealingly engage the ring member along a predetermined circumferential path extending along the inner wall surface of the ring member.

A multiple leaflet valve body means, when used, has leaflets which also have circularly curved outer peripheral edge portions which likewise are adapted to meet and sealingly engage the ring member along such a predetermined inner circumferential path, and, in addition, these leaflets each have radially extending straight edge portions that are located between circumferentially adjacent individual leaflets. The adjacent straight edge portions are adapted to abuttingly and sealingly engage one another preferably along beveled edge profiles when in the closed position.

Peripheral circular edge portions of each leaflet are preferably also further characterized by having longitudinal (relative to the ring member) curved profiles which match the adjacent inner wall curvature of the ring member when each leaflet rests in its closed position, thereby to avoid jamming of each leaflet into its associated ring member.

Each leaflet has a pair of outwardly projecting flattened ears whose body portions are preferably unitarily formed with the associated leaflet. Relative to the associated leaflet, the ears of a pair are generally oppositely disposed relative to each other and define therebetween an eccentric hinging axis. Each ear of a pair is accommodated within a different one of a pair of complementary recesses that are associated with the ring structure. Each recess is provided in an independent bearing housing that is located in and along the ring member adjacent to the central passageway thereof. Thus, the recesses and their associated bearing housings preferably coact with the ear members of a leaflet to provide a self-aligning pivotal hinging-type of spherical bearing subassembly for each leaflet.

The two flattened ears on each leaflet each have a uniform thickness that is comparable to that of their associated leaflet. This flat ear structure is, in general, in contrast to a full semi-spherical ear structure of the type found in prior art self-aligning spherical bearings. The present ear structure reduces frictional losses. Each ear is provided with edge faces which are preferably spherically curved and which wipe off blood in the associated recess with each oscillation of an associated leaflet.

The two ears on each leaflet each have spherical convex outer peripheral edge portions which rest in matching spherical concave recesses provided in the bearing housings. Small, uniform clearances between the ears and the associated recesses provide free and smooth self-aligning spherical bearing surfaces for pivotal hinging movements.

The annular valve body structure has a toroidal rigid ring member that is generally arcuate with outturned arms when viewed in radial cross-section, thereby to achieve rigidity and strength. The ring member is provided with at least one pair of circumferentially spaced holes through its mid-region side wall. The holes of each pair thereof define a common axis extending across the passageway defined by the inner side wall of the ring member. Within each hole, an independent or separate bearing housing is received that incorporates at least one recess of a self-aligning bearing subassembly.

The perimeter of each hole in the ring member is provided with an inside taper, and each bearing member is provided with a corresponding matching outside taper in its peripheral side walls. Thus, each bearing housing is adapted to fit and seat radially (relative to the ring member) from exteriorly into the associated hole, thereby to seat and form a predetermined leakproof association therebetween with each recess extending a predetermined radial distance into the ring member and the passageway therethrough. By so radially mounting each bearing housing in and through a ring member, leaflet pivot axis adjustments are possible. Also, the prior art assembly problems associated with ring member flexing are completely avoided.

Each leaflet preferably is provided with a bend that extends parallel to or along its hinging axis, thereby to enhance leaflet rigidity and strength. This bend is preferably adjusted so that, in the assembled fully open leaflet position in a given prosthesis, the bend causes the inlet (or upstream) plane portion of that individual leaflet to be substantially parallel to the central axis of the passageway of the ring structure, thereby to minimize obstruction and turbulence to the flow of blood.

The independent bearing housings also provide ease in fabrication and assembly. Appropriate materials for a particular component can be chosen with regard to its function in a single or multiple leaflet disposition. Wastage is avoided and fabrication cost is reduced. The resulting heart valve prosthesis assembly provides increased reliability and improved performance. Particularly in a multiple leaflet embodiment of a heart valve prosthesis of this invention, a virtually ideal and greatly desired unobstructed central flow of blood through the passageway of the ring structure is achievable.

Retaining means is provided to hold each bearing housing in its respective hole. Preferably, the retaining means is a band member that is comprised, for example, of a metal strip, a bundle of wires, or the like, which circumferentially extends around the outside of the ring member mid-region and over the hole regions therein to hold the bearing housings in place in their desired hole positions relative to the associated ring member.

Groove means to position a retaining band circumferentially about a bearing housing is preferably provided. A present preference is to utilize a pair of circumferentially extending (relative to the ring structure) and axially spaced (relative to the ring member and to each other) ribs provided in the back wall of each bearing housing, thereby to retain the retaining band member in position.

Stop means is preferably provided to limit radial movement of a bearing housing in its associated hole. As a present preference, circumferentially projecting rib-extensions are provided on each end of each bearing housing, thereby to provide positive stop means for each bearing housing relative to the adjacent ring structure when each bearing housing is fitted into a ring structure hole.

A heart valve prosthesis according to this invention provides unidirectional flow of blood with maximum central flow, minimal obstruction or turbulence, and minimal loss of energy. The prosthesis is preferably fabricated of selected appropriate clinically acceptable materials for individual prosthesis components, the material choice depending upon component function. The prosthesis is adapted to achieve long, reliable and efficient service. Associated reductions in cost of fabrication and assembly are possible.

For example, prosthesis components can be coated with pyrolytic carbon, or formed of titanium or other clinically acceptable metals (especially metal alloys) known to be suitable for use in a mammalian (including human) body environment. Pyrolytic carbon coatings are known to be capable of having hard and highly polished, smooth, glossy surfaces. A hard surface has high wear resistance, while a highly polished smooth glossy surface has minimum friction. Such a coated surface is desirable for fabrication of the stationary and the moving parts of a bearing. Titanium and the other clinically acceptable metals are ductile, light-weight and easy to work with; thus, such metals are suitable for use in forming a rigid body component of the prosthesis. Also, all of the materials selected with their highly polished, smooth and glossy surface have low blood clotting characteristics. The ring structure is preferably either fabricated of titanium (or other suitable metal or metal alloy), or is coated with a pyrolytic carbon material.

Contacting surface portions between the ear members and the bearing housings (including the recesses) are preferably provided with pyrolytic carbon coated material (as taught in the U.S. Pat. No. 3,526,005 or the like) which produces a hard and highly polished smooth glossy surface for long wear-resistant life and minimal frictional losses.

The inventive heart valve prostheses can achieve the highest permissible degree of operational reliability in service concurrently with significantly improved performance for unidirectional flow of blood. The foregoing defects in the prior art heart valve prostheses are believed to be generally eliminated by the heart valve prostheses of this invention.

Other and further objects, aims, features, purposes, advantages, embodiments, and the like will be apparent to those skilled in the art from the teachings of the present specification, the appended claims and the accompanying drawings.

BRIEF DESCRIPTION OF THE DRAWINGS

In the drawings:

FIG. 5 is a top plan view of another embodiment of a prosthetic heart valve assembly of this invention having a double leaflet valve flap structure, the view being taken from the upstream side with the two leaflets each being in a fully closed position;

FIG. 5A is a diametrical longitudinal (relative to the ring structure and the direction of blood flow) cross-sectional view taken along the line 5A—5A of FIG. 5, showing in phantom each leaflet in a fully open position;

FIG. 5B is a fragmentary vertical cross-sectional view taken through and along one hinging axis line 5B—5B of FIG. 5;

FIG. 9 is a top plan view of another embodiment of a prosthetic heart valve assembly of this invention having a four-leaflet valve flap structure, the view being taken from the upstream side with each of the four leaflets being shown in a fully closed position;

FIG. 9A is a diametrical cross-sectional view (relative to the ring structure and the direction of blood flow) taken along the line 9A—9A of FIG. 9, showing in phantom each of two leaflets in a fully open position;

FIG. 9B is a fragmentary vertical cross-sectional view taken through and along one hinging axis line 9B—9B of FIG. 9;

FIG. 11 is an enlarged top plan view of one of the valve leaflets of the FIG. 9 embodiment;

FIG. 11A is an enlarged side elevational view of the valve leaflet of FIG. 11 taken perpendicularly to the hinging axis (in closed position), showing in phantom the leaflet in fully open position and various angles relating to the leaflet;

FIG. 11B is an enlarged fragmentary vertical cross-sectional view taken along the hinging axis line 11B—11B of FIG. 11;

FIG. 11C is an enlarged fragmentary vertical cross-sectional view taken along line of FIG. 11C—11C of FIG. 11A;

FIG. 12 is an enlarged side elevational view of one side of one bearing housing of the FIG. 9 embodiment;

FIG. 12A is an enlarged longitudinal cross-sectional view taken along the bearing housing mid-line 12A—12A of FIG. 12;

FIG. 12B is an enlarged side elevational view of the adjacent side of the bearing housing shown in FIG. 12; and FIG. 12C is an enlarged top plan view of the bearing housing of FIG. 12 taken along the arrow V.

DESCRIPTION OF THE PREFERRED EMBODIMENTS

Figures 1, 1B:
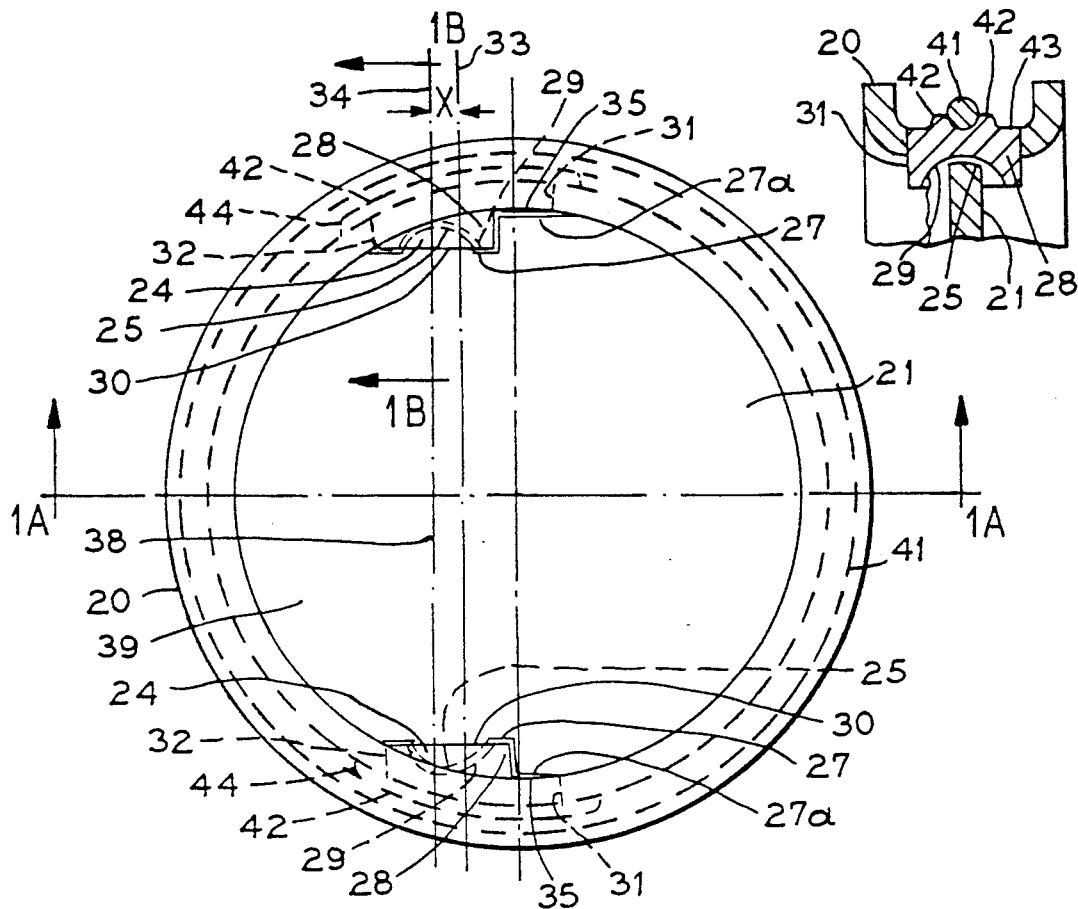
FIG. 1 is a top plan view of one embodiment of a prosthetic heart valve assembly of this invention having a single leaflet valve flap structure, the view being taken from the upstream side with its single leaflet in a fully closed position.
FIG. 1B is a fragmentary vertical cross-sectional view taken through and along the leaflet hinging axis line 1B—1B of FIG. 1.

The invention is described and illustrated with reference to specific embodiments.

Preferred embodiments of heart valve prostheses of the present invention which incorporate, successively, a single, a double and a four leaflet valve flap structure in combination with a respective associated ring structure are shown in FIG. 1 through FIG. 4B, FIG. 5 through FIG. 8B, and FIG. 9 through FIG. 12C, respectively.

In general, each leaflet of a prosthesis is provided with a pair of peripheral, opposed, flattened mounting ears. Each member ear of a pair thereof has an arcuate outer edge whose curvature preferably corresponds to a spherical segment. Each member ear is adapted for mating receipt and engagement with at least a portion of a different one of a pair of mating recesses. Each member of a recess pair has arcuate interior surface portions whose curvature preferably corresponds to a spherical segment of a sphere whose characteristics match those of the sphere associated with the curvature of the ear member arcuate edge that is engagable therewith. Each recess for the respective members of an ear pair is provided in an independent bearing housing.

Each bearing housing is preferably provided with convexly tapered peripheral side portions. The ring member that is functionally associated therewith is provided with a plurality of holes. Each hole is located along the ring member interior perimeter, and each hole has concavely tapered peripheral side portions that are adapted to receive a different bearing housing. Thus, a pair of recesses is provided for each leaflet. Each pair of recesses (one in each bearing housing) is centered along a predetermined hinging axis that extends across the ring member passageway and that is in aligned relationship with respective members of an ear pair of one leaflet when each pair of bearing housings is positioned in the holes in the ring structure. When each leaflet has its ear pair duly associated with members of the cooperating recess pair, small, uniform clearances preferably exist between each recess and adjacent portions of the associated respective ear, and preferably a fluid tight joint exists between each bearing housing and its associated ring member.

Each recess is further configured to provide a bearing surface upon which and relative to which an associated ear is self-aligning. Each leaflet with its ear pair thus duly engaged with a recess pair is allowed to swing pivotally and independently with restricted rotary oscillatory movements between an open and a closed position (inclusive). The closed position extends transversely across the passageway of the associated ring structure. These oscillatory movements occur along an eccentric, transversely extending pivoting (or hinging) axis existing across each leaflet and extending between its pair of ear members. Varying pivot excursional movements can occur during leaflet oscillations. Retaining means, such as a clamping band, hold the bearing housings in association with the ring member.

Referring to FIGS. 1 through 4B, there is seen a heart valve prosthesis having a single leaflet valve flap structure 21 and an annular structure which incorporates a ring member 20. The ring member 20 is rigid and has an annular or toroidal configuration in end (or axial) elevation and also a C-type configuration in radial longitudinal (relative to blood flow) cross-section. The mid-region 22 of the C-type configuration extends circumferentially around and defines the sidewalls of the central blood flow passageway through the ring member 20.

Figure 1A:
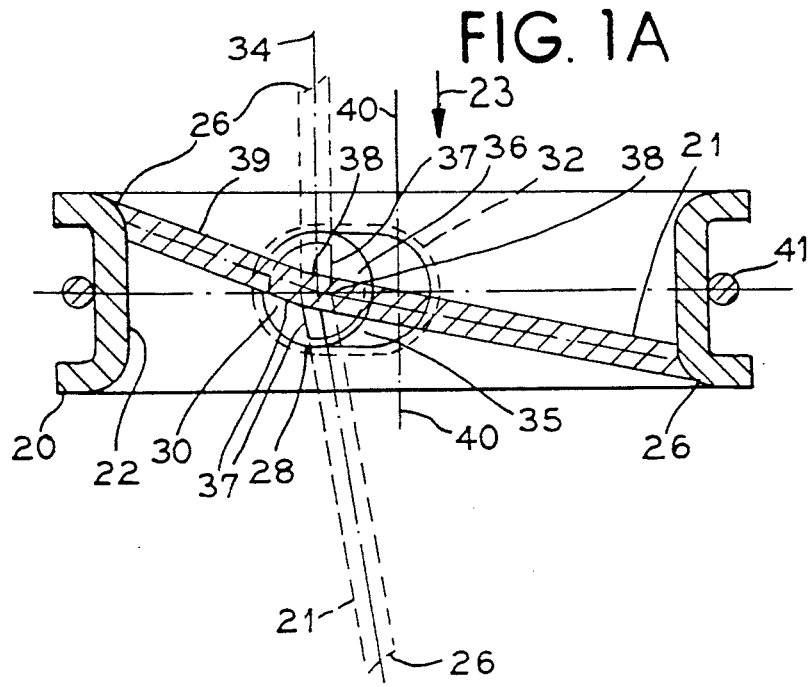
FIG. 1A is a diametrical longitudinal (relative to the ring structure and the direction of blood flow) cross-sectional view taken along the line 1A—1A of FIG. 1, showing in phantom the leaflet in a fully open position.
Figure 2:
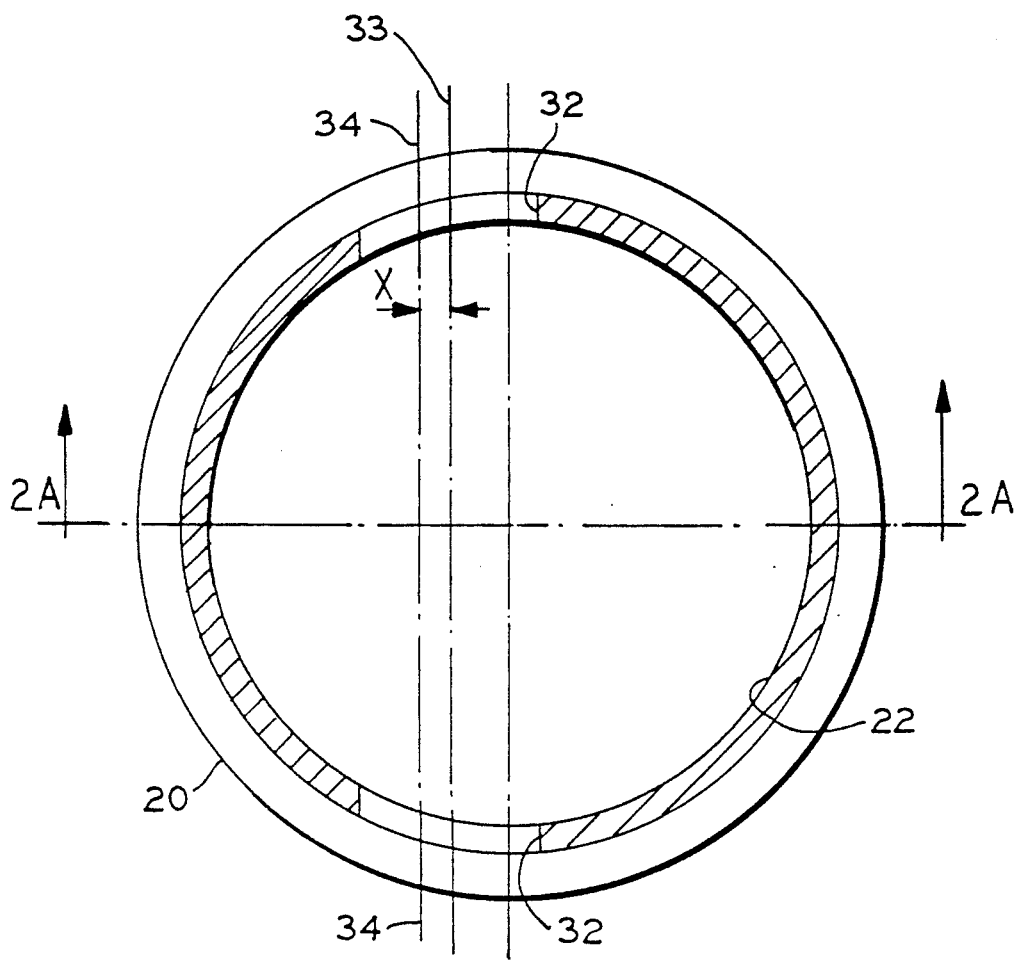
FIG. 2 is a transverse cross-sectional view taken through the mid-region of the ring structure of the FIG. 1 embodiment.
Figure 2A:
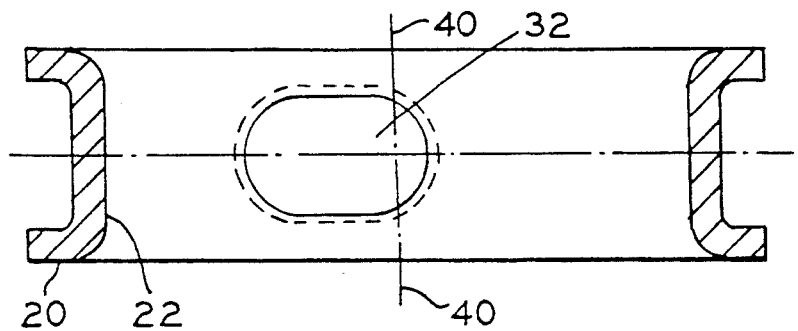
FIG. 2A is a diametrical longitudinal cross-sectional view taken along with the line 2A—2A of FIG. 2.

The leaflet 21 has a nearly circular perimeter in plan view, and it oscillates freely about an eccentric hinging axis 34 between open and closed positions (inclusive) in a restricted oscillatory rotary movement within and across the passageway of the ring member 20 in response to fluid pressure differential developed in the cardiac system of the patient in whom the prosthesis is surgically implanted with the direction of blood flow of being shown by the illustrative arrow 23. In its closed position illustrated in FIGS. 1 and 1A, the leaflet 21 fits across and covers the full cross-sectional area of the passageway through ring member 20. When in the leaflet closed position, the perimetric or peripheral edge 26 of the leaflet 21 is adjusted to seat against adjacent portions of the inner side wall 22 of the ring member 20, thereby to provide a seal preventing back flow of blood through the passageway.

The leaflet 21 has a unitarily formed pair of flattened, opposed ears 24 along portions of its peripheral edge. Each ear 24 has a spherical peripheral edge 25 and the ears 24 are disposed on nearly opposite respective side portions of the peripheral edge 26. Each ear 24 protrudes out from chordal straight edges 27 formed in leaflet 21, and each ear 24 rests in a different one of a pair of recesses 29. Each recess 29 is provided in an independently structured bearing housing 28.

Each bearing housing 28 of a pair thereof is located in the ring member 20 so as to be nearly opposite the other thereof across the passageway of the ring member 20. The recess 29 in each bearing housing 28 has side wall portions which are complementary relative to the edge 25 of the associated ear 24 and which result in the ear 24 being self-aligning therewith. In the assembled prosthesis, clearance between each ear and its associated recess are preferably small and uniform, and the leaflet 21 is freely and smoothly moveable during its oscillatory pivotal movements. The pair of bearing housings 28 functions when associated with ears 24 to retain the leaflet 21 in association with ring member 20.

Each bearing housing 28 is elongated with the elongation being in a circumferential direction relative to ring member 20 as the bearing housing 28 is mounted in a ring member 20. Adjacent one end portion of the housing body is radially (relative to ring member 20) elevated stem portion which inwardly projects into the passageway of the ring member 20 when the bearing housing 28 is mounted in the ring member 20. The stem portion has a first forward face 30 that is flat, and that extends circumferentially relative to and about the mouth of the adjacent recess 29. Each bearing housing 28 of the pair thereof is configured to be a mirror image of the other.

The side wall perimeter of the bearing housing 28 is tapered. The ring member 20 is provided with a pair of holes 32 located in the side wall 22 of the ring member 20 in an opposed relationship to each other. Each hole 32 has tapered sides that are complementary to the taper associated with the sidewall of the bearing housing 28 so as to be associatable therewith from the ring member 20 exterior. The relationship between the complementary respective tapers is such that, when a bearing housing 28 is mounted and seated in a hole 32, a fluid-tight (leakproof) joint is provided. The mounted pair of bearing housings 28 have a common axis 33 which is offset radially from a diameter or center line (C.L.) taken through the longitudinal axis 40 of the ring member 20. The leaflet 21 has a hinging (or pivot) axis 34 that is eccentrically located with respect to center line (C.L.) and that is radially further offset therefrom than is the common axis 33 of holes 32 with the distance between the common axis 33 and the hinging axis 34 being designated x (see FIG. 2).

In each bearing housing 28, the face 30 is perpendicular to the hinging axis 34 and the respective axis of each recess 29 is coaxial with the hinging axis 34. In each bearing housing 28, a second flat face 35 is provided that extends in a circumferential direction extending between the base of the stem and the opposite end portion of the bearing housing 28. Face 35 is radially (relative to axis 40) offset and in spaced, parallel, recessed relationship to first flat face 30. The faces 30 and 35 cooperate to increase the area for flow of blood through the passageway of the ring member 20 and to facilitate free and unrestricted oscillations of the leaflet 21. Like face 30, face 35 is perpendicular to the hinging axis 34.

The curvature of the peripheral edge 26 of the leaflet 21 is interrupted in the region thereof that is adjacent each face 35 of the bearing housing 28. In such a region, edge 26 is replaced in leaflet 21 by a straight edge 27a; and, also, in the region of each face 30, edge 26 is replaced by a straight edge 27. However, the mid-region of each straight edge 27 is interrupted by the outward projection therefrom of one of the flat ears 24 which are each unitary with the leaflet 21. The edges 27 and 27a of the leaflet 21 function to wipe and clean blood on the flat faces 30 and 35, respectively, with each oscillation of the leaflet 21. Each flat ear 24 has a thickness that is practically the same as that of leaflet 21.

A diametrically opposed pair of portions 36 are provided within and on opposite sides of each recess 29 in the stem portion of each bearing housing 28. Within each recess 29, the sides 37 of each portion 36 interrupt the spherical curvature of the associated recess 29 and serve to act as stop means limiting pivotal travel of each associated flat ear 24 that is seated in recess 29. Thus, the full open and full closed positions for leaflet 21 in the assembled prosthesis are determined by the circumferential sides 37 and by the side wall 22 portions of ring member 20 that are in contacting or seating relationship with portions of peripheral edge 26 of leaflet 21 when leaflet 21 is in its fully closed position. The edge 26 is provided with a profile which matches the localized profile of side wall 22 to avoid jamming between edge 26 and side wall 22 in the closed position for leaflet 21, particularly due to back pressure.

The leaflet 21 is preferably provided with a bend 38 along its hinging axis 34, thereby to give leaflet 21 rigidity and strength. The bend 38 makes the upstream plane portion 39 of the leaflet 21 extend parallel to the longitudinal central axis 40 of the ring member 20 when the leaflet 21 is in its fully open position, thereby to minimize obstruction or turbulence to the flow of blood through the passageway of the ring member 20.

The metal bearing housing retaining band 41 is provided circumferentially about the outside of the ring member 20 to hold the bearing housings 28 firmly in their respective holes 32. The band 41 is placed between two longitudinally spaced but adjacent circumferentially placed ribs 42 provided on the back face 43 of each bearing housing 28, thereby to keep the band 41 in position and to suitably accommodate a conventional suturing ring (not shown). The ribs 42 have small circumferential extensions 44 on either end of the bearing housings 28 which function to provide positive stop means for limiting radial inward movement of each bearing housing 28 when fitted into the holes 32 of the ring member 20. The band 41 is conveniently formed of a clinically acceptable metal and can have various structures.

For example, and as shown, band 41 can have a circular cross-section, thereby to fit and centrally seat it into the channel formed between the two ribs 42 on bearing housings 30. The band 41 is conveniently initially formed into a circular loop shape with adjacent open opposed ends. The band 41 is then opened a little, placed properly about ring member 20 and snugly into the channel formed between the ribs 42. The opposite two ends of the band 41 are then joined to one another by electric resistance welding or the like.

Alternatively, the band 41 can be comprised of a few turns of fine wire (not shown) of clinically acceptable metal that is wound around the ring member 20 so that the wire turns lie in the channel formed by the ribs 42. The two loose ends of the wire are engaged by a square, reef, surgical, or like knot and twisted. The twisted ends are finally preferably welded either electrically or by gas.

Referring to the drawings of FIG. 5 through FIG. 8B, there is seen another embodiment of a heart valve prosthesis of this invention which has a double leaflet (or bi-leaflet) flap disposition, and which incorporates a ring structure having a ring member 50 and two leaflets 51. The ring member 50 has a generally C-configured radial cross-section that is similar to that of the ring 20 in the single leaflet embodiment of the heart valve prosthesis, with the inner side wall 52 forming and defining the blood passageway. Each of the two leaflets 51 have a nearly semi-circular shape, oscillate freely and independently of each other about their respective eccentric hinging axes from open to closed positions (inclusive), and achieve restricted rotary movement across and within the passageway of ring member 50 in response to pressure differentials developed in the cardiac system wherein the prosthesis in implanted surgically with the direction of flow of blood being shown by the illustrative arrow 53.

Like leaflet 21, each leaflet 51 has two flattened ears 54 and each ear 54 has a peripheral edge 55 which is configured as a spherical segment. The ears 54 are disposed nearly diametrically opposite to each other on portions of a circular peripheral portion 56. Each ear 54 protrudes out from a chordal edge 57 defined in the peripheral portion 56 at locations adjacent to its radial o central straight edge 75. Preferably, the spherical edge 55 of each ear 54 so associates with a different one of a pair of recesses 59 that a minute uniform clearance exists between spherical surfaces of each recess 59 and spherical surfaces of its associated ear 54. Each recess 59 is provided in an independent bearing housing 58 which is located diametrically opposite the other thereof in the ring member 50. Each recess 59 has a curvature corresponding to a spherical segment and the recesses 59 cooperate with each other and with the ears 54 to provide self-aligning bearing assemblies for free and smooth pivotal movement of each leaflet 51 and also to retain each leaflet 51 in association with the ring member 50.

Each of the two bearing housings 58 has a flat inner or front face 60 defined adjacent to and about the mouth of each recess 59 thereof, thereby to facilitate free oscillations of each leaflet 51. Each bearing housing 58 has a tapered peripheral wall 61. Each bearing housing 58 is introduced from the outwards of ring member 50 into a hole 62 defined in side wall 52 of the ring member 50. Each hole 62 has matingly tapered sides relative to each side wall 61 to achieve a seating and sealing engagement between each bearing housing 50 that is positioned therein and ring member 50. The holes 62 are on diametrically opposite sides of the ring member 50.

The holes 62 have a common diametrical axis 63 while the hinging axis 64 of each leaflet 51 is placed eccentrically with respect to axis 63 of the ring member 50. The two hinging axes 64 are each parallel to the common axis 63 and each is spaced at a distance y (see FIG. 6) away from it on either side thereof. The holes 62 and the bearing housings 58 are made oblong relative to the circumference of ring member 50 to accommodate two bearing recesses 59 in circumferentially adjacent relationship to one another.

The planes of the common flat 60 about the mouth of each adjacent recess 59 are parallel to the planes formed by respective opposed chordal edges 57 of each leaflet 51 and perpendicular to the hinging axis 64. The chordal edges 57 are also perpendicular to the respective hinging axes 64, thereby to achieve free rotary movement of each leaflet 51. Both flat ears 54 of each leaflet 51 have practically the same thickness as that of the associated leaflet 51. Portions 66 of each recess 59 in the bearing housings 58 provide discontinuities to the recess spherical curvature and portions 66 are conveniently comprised of the material of the bearing housing 58. Portions 66 serve to avoid potential stagnation of blood which would otherwise occur in unused portions of the cavities of the recesses 59, due to the indicated restricted rotary movement of the leaflets 51. The sides 67 of the filled-in portions 66 act as stop means for limiting pivotal travel of the ears 54. Consequently, the leaflets 51 have their desired end positions at locations of maximum opening and closing. Inner side portions of the wall 52 of the ring member 50 also serve as additional stop means for the leaflets 51 in their respective closed positions. The outer peripheral circular edges 56 of the two leaflets 51 each have a curved profile which is matched relative to the curvature of the inner wall 52 at locations where portions of edges 56 rest, thereby to avoid jamming between the edges 56 and the wall 52, particularly due to back pressure that may occur in the leaflet 51 closed position during use of the prothesis.

Each leaflet 51 is preferably provided with a bend 68 along its hinging axes 64, thereby to give it rigidity with strength. The bends 68 make upstream plane portions 69 of each of the leaflets 51 parallel to the central longitudinal axis 70 of the ring member 50 when each leaflet 51 is in its fully open position, thereby to minimize obstruction and turbulence to the central flow of blood through the passageway of the ring member 50.

A metal band 71 is provided from outside on the ring member 50 to hold the bearing housings 58 firmly in the holes 62. The band 71 is placed between two circumferentially extending longitudinally spaced ribs 72 provided on the back face 73 of each bearing housing 58 both in order to keep the band 71 in position and also to accommodate a conventional suturing ring (not shown) suitably. The ribs 72 have short circumferential extensions 74 at opposite ends of each bearing housing 58 to serve as positive stop means limiting radial travel of each bearing housing 58 into the ring member 50 when they are fitted into the respective holes 62.

Each leaflet 51 has a substantially semi-circular perimeter 56 so as to cover about half of the area of the passageway through the ring member 50. The perimeter edges 56 of each leaflet 51 meet the inner side wall 52 of the ring member 50 and are configured to provide a peripheral seal against the flow of blood when in their closed positions. The radially extending straight edge portion 75 of each leaflet 51 at the end of each curved peripheral edge 56 have a beveled profile 76 that abuts against the straight edge portion 75 of the adjacent leaflet to provide seating engagement and a leakproof joint 77 therebetween against backflow of blood when the leaflets 51 are in their closed positions. The flat chordal edges 57 of the leaflets 51 from where the ears 54 protrude out are each at right angles both to the straight radial edges 75 of each leaflet 51 as well as to the respective hinging axes 64, thereby to clean blood on the flat faces 60 of the bearing housings 58 during each oscillation of the leaflets 51. The spherically curved peripheral edge 55 of each ear 54 sweeps the adjacent spherical surfaces of each recess 59.

Referring to the drawings of FIG. 9 through FIG. 12C, there is seen another embodiment of a heart valve prosthesis of this invention which has a four leaflet flap disposition and which incorporates an annular structure having a ring member 80 and four leaflets 81. The ring member 80 has a generally C-configured radial cross-section that is similar to that of the ring member 20 or the ring member 50. Inner side wall 82 of ring member 80 defines a central blood passageway.

The four leaflets 81 each have approximately a quarter-circular configuration. Each leaflet 81 oscillates freely and independently of all others about its own eccentric axis between open and closed positions (inclusive); and each leaflet achieves restricted rotary movement within the passageway of ring member 80 in response to pressure differentials developed in the cardiac system wherein the prosthesis is implanted surgically with the direction of flow of blood being shown by the illustrative arrow 83. Each leaflet 81 has two flat ears 84 and each ear 84 has a peripheral edge 85 which is preferably configured as a spherical segment. The ears 84 are disposed at circumferentially spaced 90° intervals about the passageway through ring member 80. Each leaflet 81 has a circular periphery 86 that extends between chordal straight side edges 87, and each leaflet 81 has straight radially extending edges 105 that extend from the side edges 87 and also lie adjacent to the side edges 87 of the adjacent leaflets 81 in the closed position. Each ear 84 rests in a different one of two matching spherical recesses 89 preferably with minute uniform clearances therebetween. Each recess 89 is provided in an independent bearing housing 88 and each housing 88 is equally circumferentially spaced from the others thereof at 90° centers distributed about the ring member 80 in side wall 82. Each bearing housing 88 has two incorporated complimentary spherically sided recesses 89. One recess 89 of each housing 88 coacts with a recess in a circumferentially adjacent housing 88 to provide a recess pair for holding and pivotally supporting each leaflet 81 in self-aligning bearings in combination with that leaflets pair of ears 84, thereby to achieve free and smooth pivotal movement of each leaflet 81, and also to provide retaining means for each ear 84. Each of the four bearing housings 88 has two recesses 89 therein and also two flat faces 90, one about each recess 89 mouth. Each face 90 in a housing 88 is perpendicular to other and the axis of each recess 89 is oriented perpendicularly relative to the other in a housing 88. Each housing 88 has tapered peripheral side walls 91.

The longitudinal mid-region of wall 82 of the ring member 80 is provided with rectangularly sided, tapered holes 92 at 90° equally spaced intervals. Each hole 92 perimeter matches the profile of a bearing housing 88. Each housing 88 is seated from the outside of ring member 80 into a hole 92 to form a leakproof joint. The two pairs of diametrically opposite holes 92 have two common diametrically extending (relative to ring member 80) axes 93 located at right angles to each other, while the hinging axis 94 of each of the four leaflets 81 (though which axis each pair of ears 84 extends) is placed eccentrically with respect to a pair of diametrical center axes of the ring member 80 that intersect at 90° relative to each other so that the hinging axes form a chordal square arrangement across passageway of the ring member 80 with the two common axes 93 forming the square diagonals. The holes 92 and the bearing housing 88 are made circumferentially oblong relative to the ring member 80 thereby to accommodate two bearing recesses 89 in each housing 88.

The axis of each recess 89 is disposed and oriented to be coaxial with the pivoting axis 94 of each leaflet 81. Both ears 84 of each leaflet 81 have practically the same thickness as that of the associated leaflet 81. Portions 96 of each recess 89 in each bearing housing 88 are not spherically defined and are in effect filled-in to avid what would otherwise be potential stagnation of blood in unused cavities of each recess 89 caused by the restricted rotary movement of the leaflets 81. The sides 97 of the filled-in portions 96 act as stop means for the ears 84 and also define end positions for the leaflets 81 at their respective desired positions of maximum closing and opening. Inner side wall portions 82 of the ring member 80 also serve as additional stop means for the peripheral circular edges 86 of the leaflets 81 in their respective closed positions. The peripheral circular edges 86 of each of the our leaflets 81 have matching curved profiles relative to the corresponding inner wall 82 curvature of ring member 80 particularly where the edges 86 abut when in the closed leaflet position, thereby to avoid jamming between the edges 86 and the wall 82 when the leaflets 81 are in the closed position.

Each leaflet 81 is preferably provided with a bend 98 that extends along its respective hinging axis 94 to give the leaflets 81 rigidity with strength. The bends 98 make the upstream plane portions 99 of the leaflets 81 parallel to central longitudinal axis 100 of the ring member 80 when the leaflets 81 are each in their fully open position, thereby to minimize obstruction and turbulence to the flow of blood through the passageway of the ring 80.

A metal band 101 is provided around the outside on the ring member 80 to hold the bearing housings 88 firmly in their respective positions in the holes 92. The band 101 is placed between two circumferentially extending, longitudinally spaced ribs 102 that are preferably provided on the face 103 of each of the bearing housings 88 to keep the band 101 in position and to suitably accommodate a conventional suturing ring (not shown). The ribs 102 have short circumferential extensions 104 on either end of each bearing housing 88 to form positive stop means for the bearing housings 88 when they are fitted into the holes 92.

Since it has substantially a quarter-circular shape, each leaflet 81 is adapted to cover about a quarter area of the passageway through the ring member 80. The peripheral circular edges 86 of each of the four leaflets 81, each of which meets the inner side wall 82 of the ring member 80, provide a peripheral seal to the flow of blood when in the closed position. The radially extending straight side edge portions 105 of each leaflet 81 have beveled profiles 106 that abut against the side portions 105 of circumferentially adjacent leaflets 81 to provide four leakproof straight radially extending joints 107 therebetween, thereby preventing the backflow of blood in the closed valve position of the heart valve prosthesis.

The straight chordal edges 87 of the leaflets 81 at locations where the ears 84 extend outwardly are at an angle relative to the radial edges 105, but are perpendicular to the respective hinging axis 84 and also parallel to the faces 90, thereby to clean blood on the flat faces 90 of the bearing housings 88 during each oscillation of the leaflets 81.

Simultaneous full opening capability for each of the four leaflets 81 makes for a virtually ideal and much desired unobstructed central flow of blood through the passageway member 80 in this four leaflet embodiment of the heart valve prosthesis.

Component Number Identification in the Drawings:

| Single Leaflet | Double Leaflet | Four Leaflet | Description |
|---|---|---|---|
| 20 | 50 | 80 | Ring member |
| 21 | 51 | 81 | Leaflet |
| 22 | 52 | 82 | Inner side wall of the ring member |
| 23 | 53 | 83 | Arrow showing direction of flow of blood |
| 24 | 54 | 84 | Flat ears of each leaflet (paired) |
| 25 | 55 | 85 | Spherical edge of one ear |
| 26 | 56 | 86 | Peripheral edge portion of a leaflet |
| 27/27a | 57 | 87 | Chordal or side edge portion of a leaflet |
| 28 | 58 | 88 | Independent bearing housing |
| 29 | 59 | 89 | Spherical recess in a bearing housing |
| 30 | 60 | 90 | Flat face of a bearing housing |
| 31 | 61 | 91 | Tapered side wall of a bearing housing |
| 32 | 62 | 92 | Tapered hole in side wall of the ring member |
| 33 | 63 | 93 | Common axis of the ring member paired holes |
| 34 | 64 | 94 | Hinging axis of leaflet |
| 35 | — | — | Auxiliary flat face on bearing housing |
| 36 | 66 | 96 | Closed or filled-in portion of the recess |
| 37 | 67 | 97 | Side of the closed portion |
| 38 | 68 | 98 | Bend in the leaflet |
| 39 | 69 | 99 | Upstream plane portion of the leaflet |
| 40 | 70 | 100 | Central longitudinal axis of the ring member |
| 41 | 71 | 101 | Metal band |
| 42 | 72 | 102 | Two ribs on the bearing housing back wall |
| 43 | 73 | 103 | Back wall of the bearing housing |
| 44 | 74 | 104 | Small circumferential rib-extensions |
| — | 75 | 105 | Radial straight edge of the leaflet |
| — | 76 | 106 | Bevel profile on the straight edge of the leaflet |
| — | 77 | 107 | Leak proof joint |
| C.L. | C.L. | C.L. | Center Line (diameter) |

Figure 3:
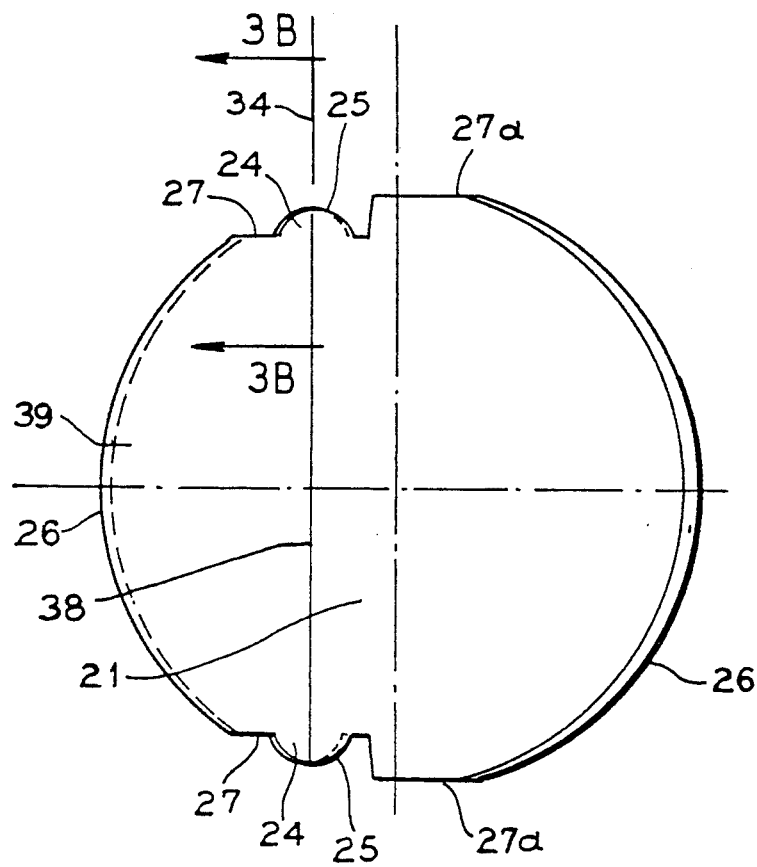
FIG. 3 is a top plan view of the valve leaflet of the FIG. 1 embodiment.
Figure 3B:
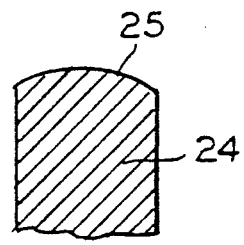
FIG. 3B is an enlarged fragmentary vertical cross-sectional view taken along the hinging axis line 3B—3B of FIG. 3.
Figure 3A:
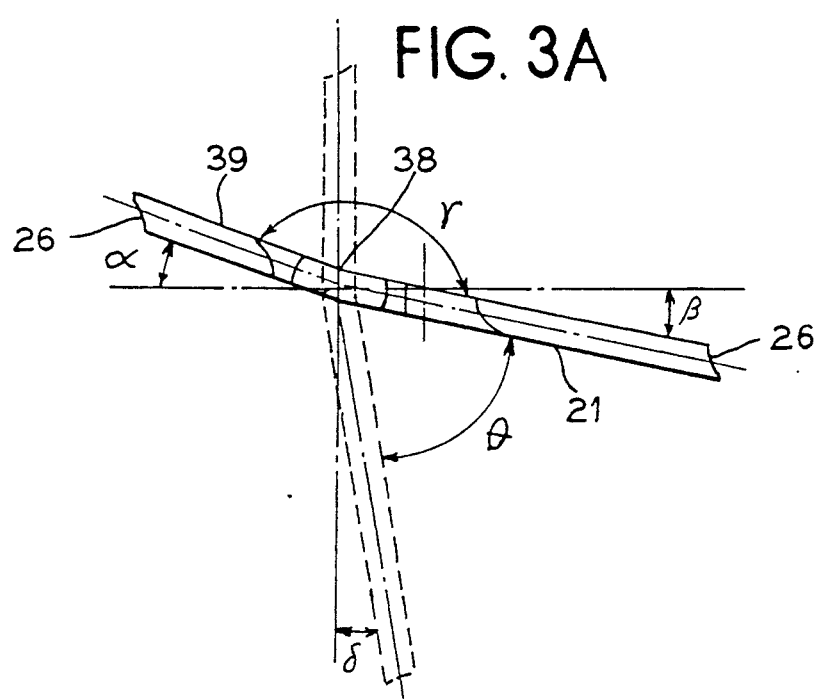
FIG. 3A is a side elevational view of the valve leaflet of FIG. 3 taken perpendicularly to the hinging axis in closed position, showing in phantom the leaflet in fully open position and various angles related to the leaflet.
Figure 4:
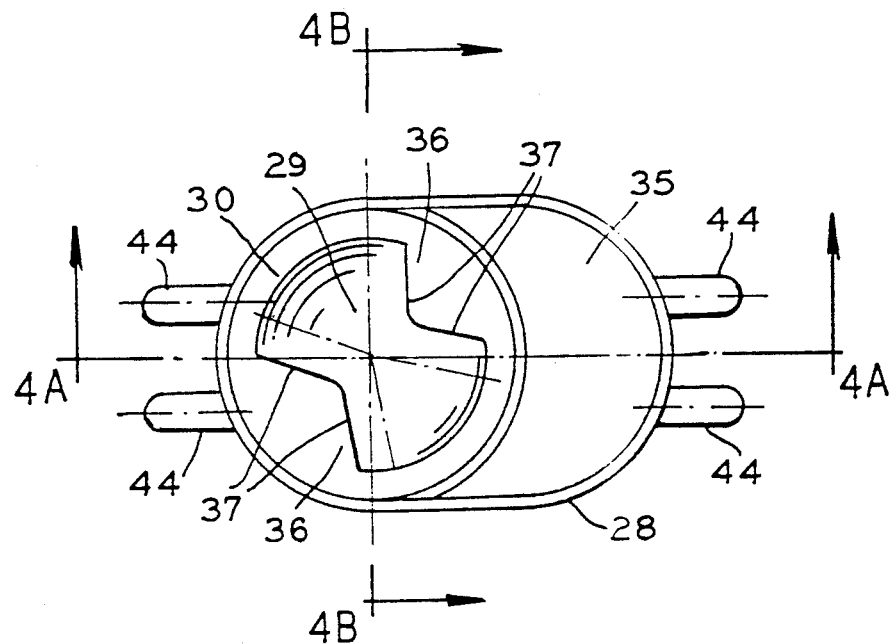
FIG. 4 is an enlarged top plan view of one bearing housing of the FIG. 1 embodiment.
Figure 4A:
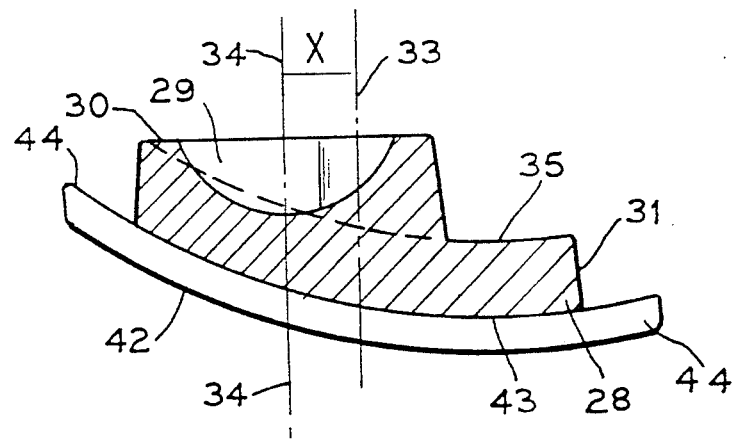
FIG. 4A is an enlarged longitudinal cross-sectional view taken along the bearing housing mid-line 4A—4A of FIG. 4.
Figure 4B:
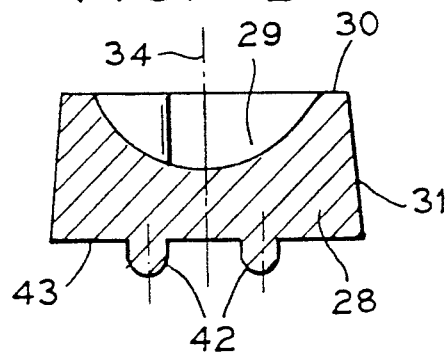
FIG. 4B is an enlarged transverse cross-sectional view taken along the recess center line 4B—4B of FIG. 4.
Figure 6:
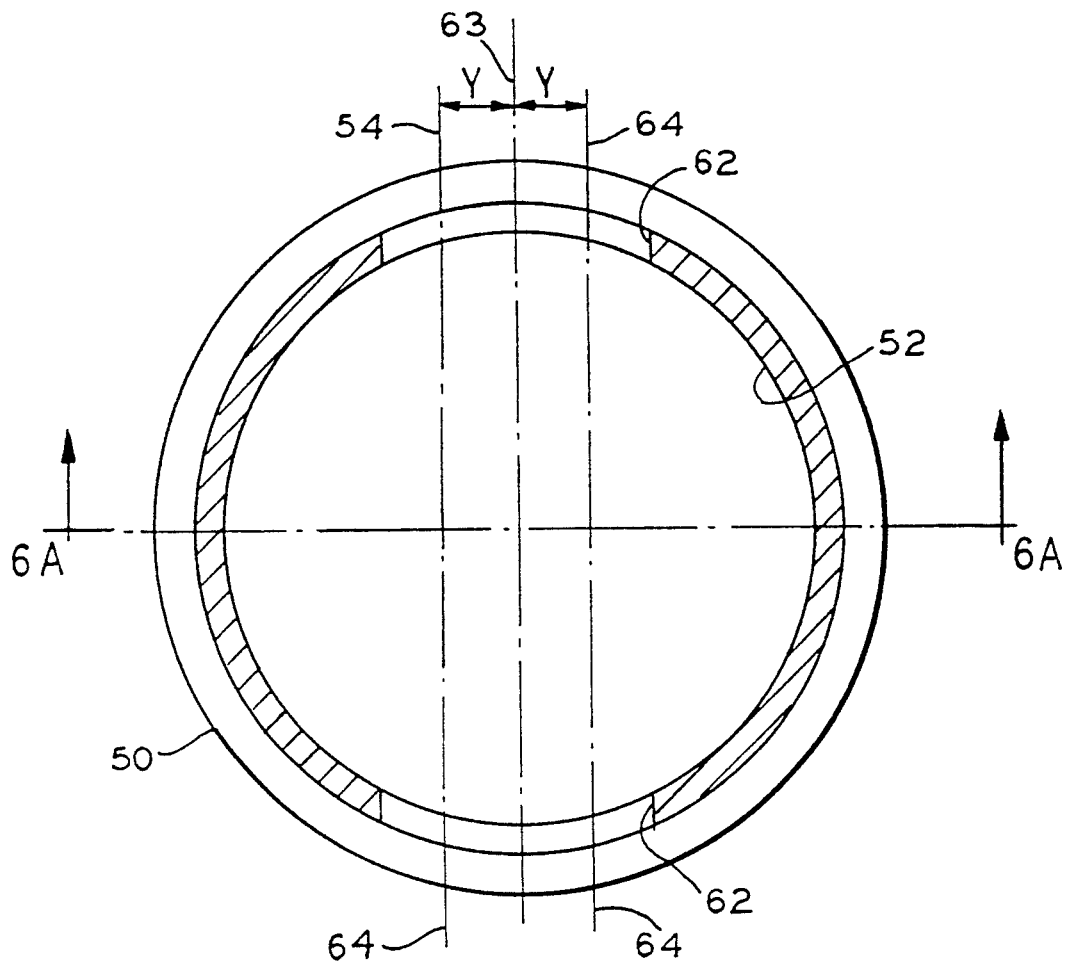
FIG. 6 is a transverse cross-sectional view taken through the mid-region of the ring structure of the FIG. 5 embodiment.
Figure 6A:
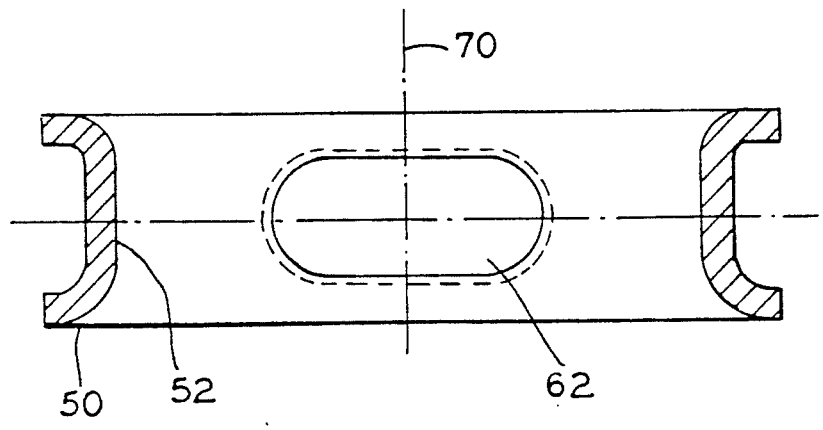
FIG. 6A is a diametrical longitudinal cross-sectional view taken along the line 6A—6A of FIG. 6.
Figure 7:
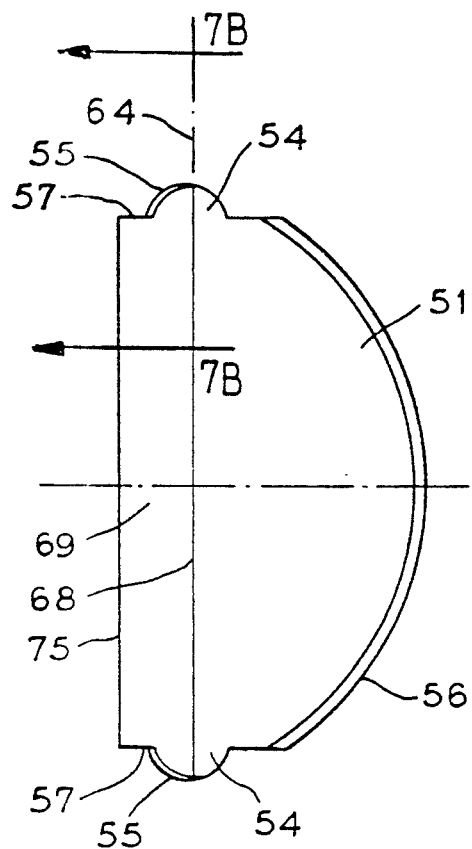
FIG. 7 is a top plan view of one of the valve leaflets of the FIG. 5 embodiment.
Figure 7B:
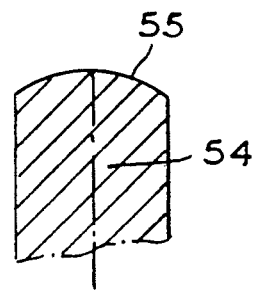
FIG. 7B is an enlarged fragmentary vertical cross-sectional view taken along the hinging axis line 7B—7B of FIG. 7.
Figure 7A:
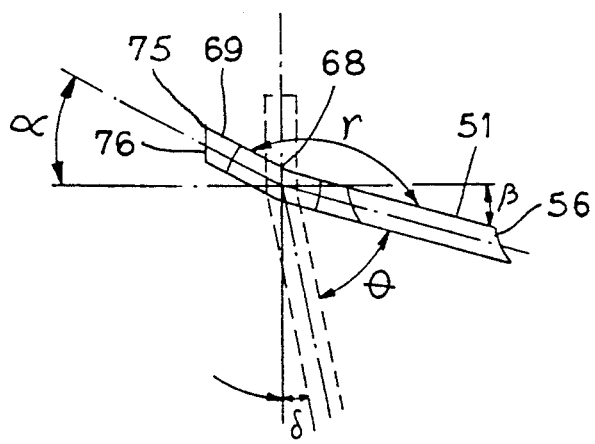
FIG. 7A is a side elevational view of the valve leaflet of FIG. 7 taken perpendicularly to the hinging axis in closed position showing in phantom the leaflet in fully open position and various angles related to the leaflet.
Figure 8:
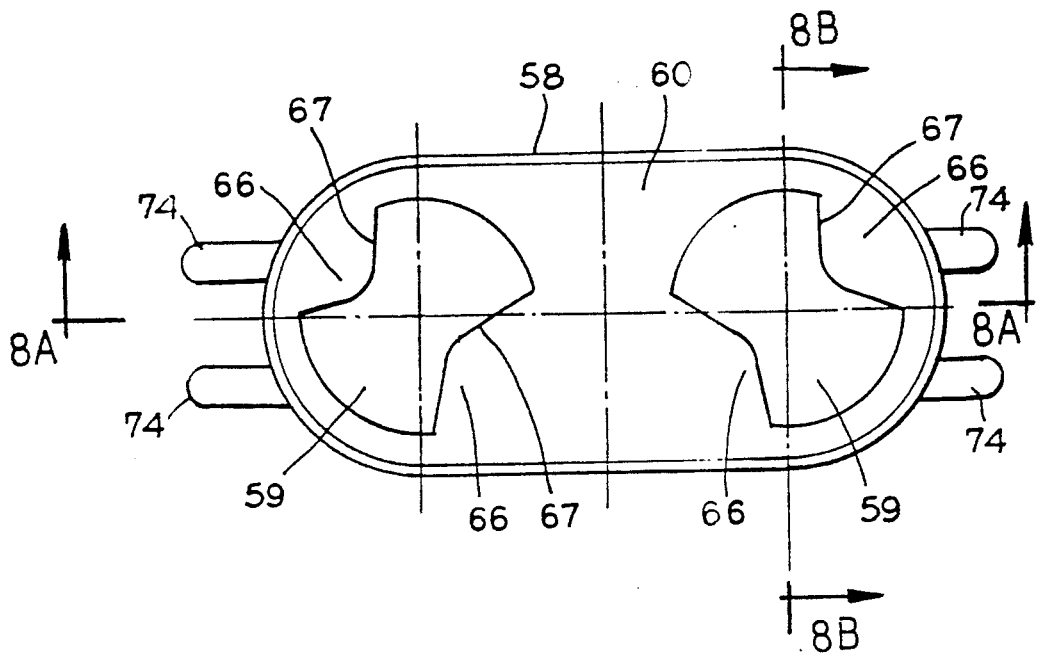
FIG. 8 is an enlarged top plan view of one bearing housing of the FIG. 5 embodiment.
Figure 8A:
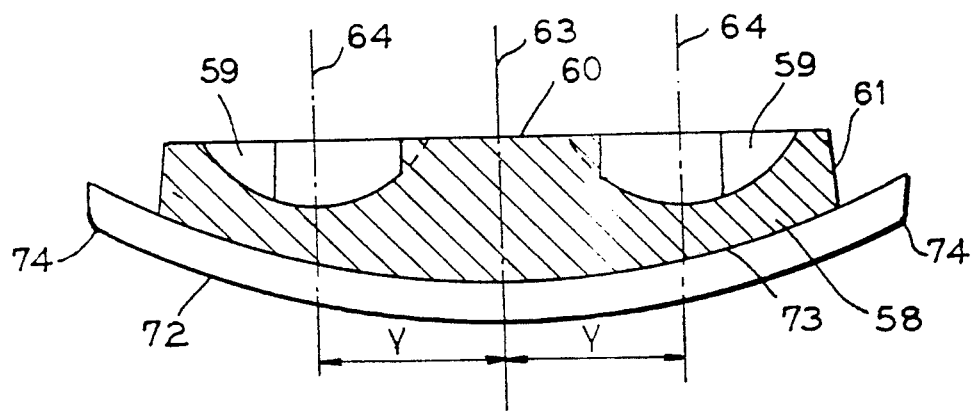
FIG. 8A is an enlarged longitudinal cross-sectional view taken along the bearing housing mid-line 8A—8A of FIG. 8.
Figure 8B:
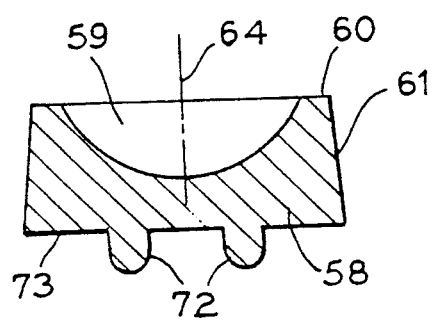
FIG. 8B is an enlarged transverse cross-sectional view taken along the recess center line 8B—8B of FIG. 8.
Figure 10:
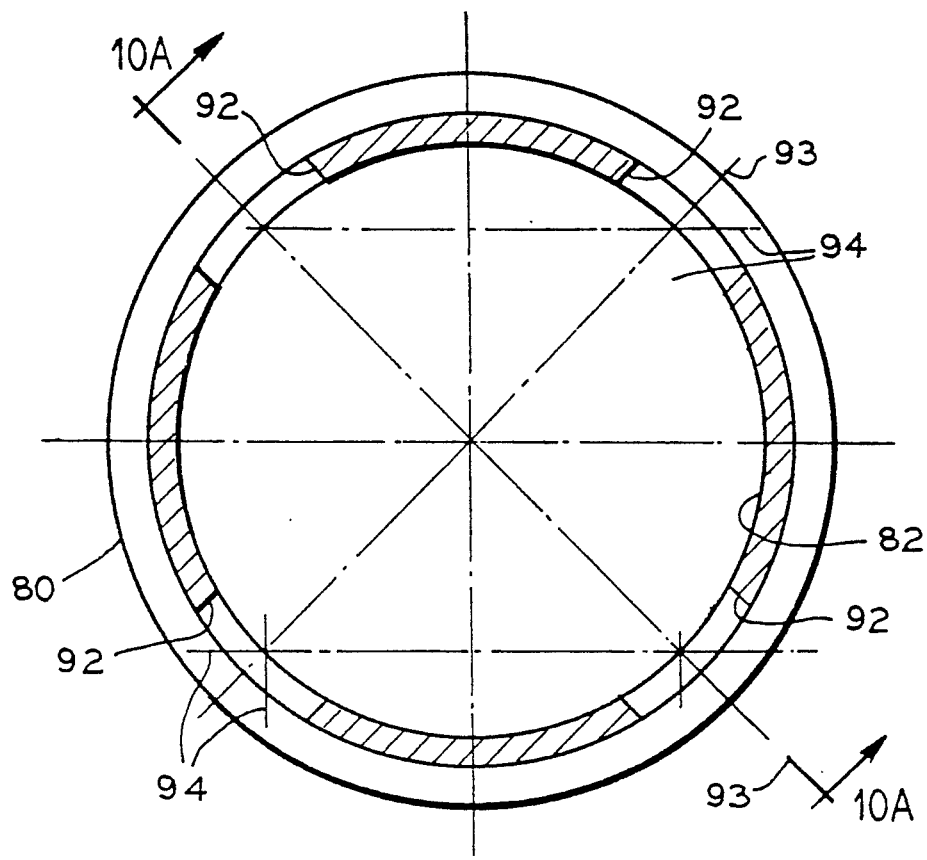
FIG. 10 is a transverse cross-sectional view taken through the mid-region of the ring structure of the FIG. 9 embodiment.
Figure 10A:
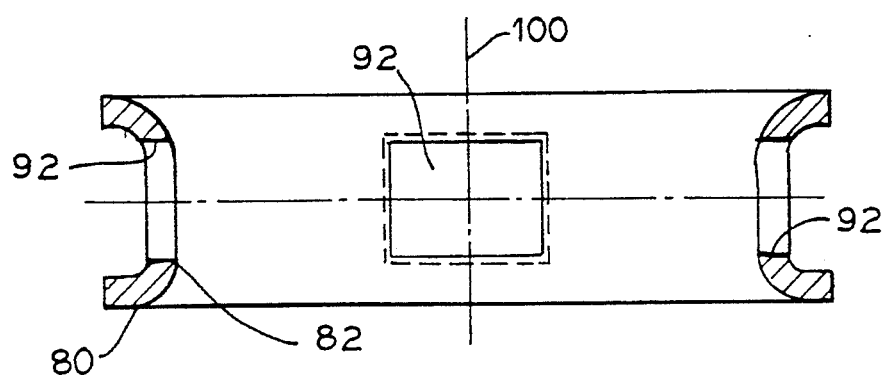
FIG. 10A is a diametrical longitudinal cross-sectional view taken along the line 10A—10A of FIG. 10.

As will be appreciated from the foregoing description, each leaflet in its fully open position in an assembled valve prosthesis assembly of this invention preferably retains its inlet or up-stream plane portion parallel to the central axis of the ring member to minimize obstruction and turbulence to the flow of blood. At the same time, in such fully open position, the outlet or down-stream plane portion of a leaflet is preferably inclined by an angle $\delta$ to the central axis of the associated ring member. This inclination is towards the closing position of a valve assembly. An angle $\Theta$ is the excursion through which a leaflet rotates from open to closed positions and vice versa. Thus, $\delta + \Theta + \beta = 90°$ where $\beta$ is an angle which the down-stream portion of the leaflet makes with horizontal plane of the associated ring member when the leaflet is in its closed position (see FIGS. 3A, 7A and 11A).

This inclination angle $\delta$ makes a valve self-closing and also facilitates closing of a valve when pressure of blood in a receiving or distal chamber or compartment of heart increases. As a matter of fact, in the case of a mitrally located valve, the down-stream portion of the leaflet goes on floating in the receiving chamber as it gets filled with blood and eventually the leaflet closes the valve completely due to rise in pressure (back-pressure) during left ventricular contraction, and, thus, the valve acts as non-return valve or one-way check valve.

If the down-stream portion of a leaflet remains parallel to the central axis of the associated ring member in the fully open position of the valve, the leaflet is believed not to close at all.

The inclination by angle $\delta$ of the down-stream portion of a leaflet in its fully open position is maintained between about 5° to 10° in single and bi-leaflet heart valves while this angle is between about 15° to 25° in a four or multiple leaflet heart valve prothesis. In the closed position of a valve, the downstream plane portion of a leaflet is also made to rest at an angle $\beta$ relative to the horizontal plane of the associated ring member so that the angle $\Theta$ through which the leaflet rotates from fully closed to fully open position reduces as the angle $\beta$ or the angle $\delta$ or both increase ($\delta + \Theta + \beta = 90°$), thereby facilitating early opening or closing of the valve.

In general, the smaller the angle $\delta$ of the inclination of down-stream portion of a leaflet in a fully open position of a valve, the lesser the obstruction encountered for flow of blood, but, at the same time, more time is required for closure of the leaflet since it has to rotate through a greater angle $\Theta$ for closure of the valve.

The inlet plane portion of a leaflet rests at an angle $\alpha$ with respect to the horizontal plane of an associated ring member in the closed position of a valve while in the fully open position the leaflet is parallel to the central axis of the ring member or at right angles to the horizontal plane.

Thus, the relationship between leaflet tilt angles is: $90° - \alpha = \Theta$. Similarly, $\gamma = 180° - \alpha + \beta$ or $= 90° + \Theta + \beta$ or $\delta = 180° - \gamma$. Since $\beta + \Theta + \delta = 90°$, therefore, $\Theta = \gamma - \beta - 90°$ where $\gamma$ is the included bend angle of the leaflet.

(a) It provides additional rigidity with strength to the leaflet and to the ears,
(b) It provides higher efficiency in quick opening or closing of the valve by adjusting the bend angle $\gamma$; and
(c) It provides laminar flow and minimizes or obviates turbulence when the up-stream side plane of the leaflet is placed parallel to the central axis of the ring member in fully open position by adjusting the bend angle $\gamma$. Since the prosthetic heart valves of this invention are preferably to be made available in different sizes varying from about 17 mm to 33 mm in diameter of the ring member and with different dispositions of their leaflets, such as a single leaflet or multiple leaflet including bi-leaflet, the included bend angle $\gamma$ preferably varies between about 155° to 170°.

From the foregoing description, it will also be appreciated that the well established principle of "self-aligning spherical bearing" is made use of in the leaflet hinging mechanism employed in this invention. Thus, the ears are flattened to reduce frictional losses in bearings. The flattened ear edge and chordal edge wipe-off the bearing recess and the flat face at the mouth of the bearing recess, respectively. To have smooth movement with the least effort, or to achieve minimal loss of energy in oscillations of the leaflet, close end tolerances are very much preferred, and such tolerances are easily achievable in the practice of this invention.

Further, by providing a bend at the ears, stability of the bearing mechanism is increased without increasing mating area in the bearings which is believed to be directly responsible for frictional loss in a the self-aligning spherical bearing.

From the foregoing description it will also be appreciated that the C-type cross-sectional profile used in the ring member that is incorporated into a valve assembly of this invention is mainly for rigidity which is very much preferred for maintaining close tolerance in the bearing mechanism at all times. The bell type mouth for inlet and outlet gives smooth entry and exit or discharge of blood respectively. The central straight wall portion of the ring member, which is used to mount bearing housings frm outside, allows the rib extensions to rest properly when inserted from an exterior location. It also permits the band location to be centrally positioned in the groove of the C-type section leaving sufficient space on both sides of the band to accommodate a suturing skirt. Both side curvatures of C-type ring member and of the band do not allow the suturing skirt to slip.

The rigid ring member having C-type cross-sectional profile gives smooth flow of blood. A ring member with such a configuration can be produced if desired from sheet metal inexpensively, or from pyrolytic carbon coated material with hardly any breakage in its manufacture or i assembly.

Also, just by changing the location and the size of the holes in the ring member, various type of dispositions for a leaflet, such as a single leaflet or multiple leaflet arrangement, including a bi-leaflet prosthetic heart valve, can be produced.

From the foregoing description, it will also be appreciated that the independent bearing housings which can be introduced into a ring member from outside facilitate: (a) easy assembly, (b) minimal or no breakage of the ring member during assembly, if it is fabricated from pyrolytic carbon coated material, (c) maximizing required or desired engagement of the self-aligning spherical bearing components (male and female), resulting in reliable and long term (or several years) of trouble-free service which is a time interval that is expected to outlive the span of human life, and (d) achievement of closed end-play tolerance in the bearing by selective assembly resulting in smooth oscillations of the leaflets with minimal loss of energy in the oscillation, thereby to prevent or to obviate possible wobbling and resulting in superior performance.

It will be appreciated that providing the bend at the hinging axis of the leaflet gives rigidity with strength to the leaflet and also to both ears on the leaflet. Also, with the up-stream portion of the leaflet being parallel to the central axis of the ring member, the flow of blood is essentially laminar with minimal or no turbulence, with down-stream portion concurrently being non-obstructive, thereby permitting smooth flow of blood. In addition, inclination of the down-stream portion of the leaflet towards its closing position promotes early or quick closing of a valve by adjusting the bend angle of the leaflet and resulting in improved efficiency of the valve.

It will also be appreciated that provision of a profile at the periphery of the leaflet, where it rests when in the closed position, and the bevel straight edge of the leaflet, prevents leakage through the valve and jamming of the leaflet as a result of back pressure.

It will also be appreciated that provision of a bend to the ears gives them rigidity with strength, and also increases stability of the bearing mechanism without increasing frictional area between male and female components of the self-aligning spherical bearing, which area is believed to be directly responsible for frictional loss.

It will also be appreciated that provision of ribs at the back of the bearing housings keep the retaining band in the central position in the exterior groove of the ring member. The circumferential rib extensions act as positive stop means for inward movement of the bearing housing in the central hole on the ring member.

It will also be appreciated that the C-type cross-section of the ring member allows smooth flow of blood therethrough and keeps the ring member rigid, thereby to maintain the close tolerances of the bearing within limits which is very much preferred for smooth working of the bearing mechanism for a very long time period. Further, the C-section does not allow the suturing skirt to slip.

Various other and further embodiment applications, structures and the like will be apparent to those skilled in the art from the teachings herein provided and no undue limitations are to be drawn therefrom.

What is claimed is:

1. A prosthetic heart valve assembly comprising:
   (a) an annular structure having a central passageway with a longitudinal axis; and
   (b) flap means disposed across said passageway and pivotable in response to fluidic pressure variations applied on an upstream side thereof for achieving one way fluid flow through said passageway;
   said flap means comprising at least one leaflet means that in a fully closed position generally extend(s) across said passageway; and each individual said leaflet means having a pair of outwardly extending ear members along respective outer peripheral portions, each said pair of ear members defining therebetween a pivot axis across their associated said leaflet means, each said leaflet means being bent along said pivot axis and having a flat configuration on each side of said pivot axis;
   said annular structure comprising a rigid ring member having in cross-section a C-type configuration with a mid-region and integral radially outturned longitudinally opposite ends and with a circumferentially extending inner face and a circumferentially extending outer face and also having defined in said mid-region at least two circumferentially spaced holes that radially extend through said ring member, each said hole having sides that are radially inwardly tapered; at least two separate bearing housings each one having recess means defined in a circumferentially forward face thereof, having circumferentially extending groove means defined in a circumferentially rearward face thereof, and also having radially tapered side walls that are nestably and sealingly seated within a different one of said holes, there being one said recess means for pivotally receiving and holding each said ear member, and also one said hole for each said bearing housing; and band retaining means extending circumferentially completely around said outer face in said mid-region and engaged with said groove means of each said so seated bearing housing for holding said bearing housings in said holes;

and the interrelationship between said flap means and said annular structure being such that each said leaflet means is pivotable between fully open and fully closed positions across said passageway with said ear members each being pivotably associated with a different one of said recess means such that, when each said leaflet means is in said open position, one said side thereof is parallel to said longitudinal axis while the other said side thereof is inclined towards said longitudinal axis and towards said fully closed position; and edge portions of said ear members and of said leaflet means adjacent thereto wipe adjacent facial portions of said recesses and of said bearing housings adjacent thereto during pivotal movements of each said leaflet means.

2. The assembly of claim 1 wherein said flap means seals said passageway when in said closed position.

3. The assembly of claim 1 wherein said leaflet means comprises a single leaflet.

4. The assembly of claim 1 wherein said leaflet means comprises a pair of leaflets, each one having about a semi-circular configuration.

5. The assembly of claim 1 wherein said leaflet means comprises four leaflets, each one having about a quarter-circular configuration.

6. The assembly of claim 1 wherein peripheral edge portions of said ear members and side wall portions of said recesses each have corresponding mating spherical curvatures.

7. The assembly of claim 1 wherein said forward face of each said bearing housing adjacent each said recess means is flattened and said leaflet means is flattened in adjacent edge portions thereof.

8. A prosthetic heart valve assembly comprising:
(a) an annular structure having a central circular passageway with a longitudinal axis; and
(b) flap means disposed across said passageway and pivotable in response to fluidic pressure variations applied on an upstream side thereof for achieving one way fluid flow through said passageway;
said flap means comprising a single leaflet member that generally extends across said passageway; and a pair of opposed, flat outwardly extending ear members along respective outer peripheral portions of said leaflet member and defining therebetween an eccentric pivot axis extending across said passageway for said leaflet member, said leaflet member being bent along said pivot axis and having a flat configuration on each side of said pivot axis;
said annular structure comprising a rigid ring member having in cross-section a C-type configuration with a mid-region and integral radially outturned longitudinally opposite ends and with a circumferentially extending inner face and a circumferentially extending outer face and also having defined in said mid-region a pair of holes that radially extend through said ring member, each said hole with sides that are radially inwardly tapered; a pair of separate bearing housings, each one having a recess means defined in a circumferentially forward facial portion thereof having circumferentially extending groove means defined in a circumferentially rearward face thereof, and also having radially tapered side walls that are nestably and sealingly seated within a different one of said holes, said holes and said bearing housings cooperating with one another so that each said recess means is coaxial with said pivot axis; and band retaining means extending circumferentially completely around said outer base in said mid-region and engaged with said groove means of each of said so seated bearing housings for holding said bearing housings in said holes, said retaining means being located on external circumferential portions of said ring member; and the interrelationship between said flap means and said annular structure being such that each one of said ear members is pivotally associated with and retained by a different one of said recess means so that said leaflet member is pivotable between a fully open position and a fully closed position across said passageway with said ear members each being associated with a different one of said recess means such that, when said leaflet member is in said open position, one said side thereof is parallel to said longitudinal axis and the other said side thereof is inclined towards said longitudinal axis and towards said fully closed position; and edge portions of said ear members and of said leaflet member adjacent thereto wipe adjacent facial portions of said recess means and of said bearing housings adjacent thereto during pivotal movements of said leaflet member.

9. The assembly of claim 8 wherein said single leaflet member seals said passageway when in said closed position.

10. The assembly of claim 8 wherein peripheral edge portions of said ear members and side wall portions of said recesses each having mating spherical curvatures.

11. The assembly of claim 8 wherein said recesses exist only in quadrants over which said ear member edge portions pass when said leaflet member moves between said open and said closed positions.

12. The assembly of claim 8 wherein said forward facial portions are flat and extend perpendicularly to said pivot axis and wherein said leaflet member is flattened in adjacent edge portions thereof so that said adjacent flattened edge portions wipe said flat forward facial portions when said leaflet member pivots.

13. The assembly of claim 12 wherein circumferential channel means is defined in rearward facial portions of each said bearing housing wherein said band means extends.

14. The assembly of claim 8 wherein each said bearing housing includes stop means limiting radial movement of said bearing housing into said passageway through said respective associated hole.

15. A prosthetic heart valve assembly comprising:
(a) an annular structure having a central circular passageway with a longitudinal axis; and
(b) flap means disposed across said passageway and pivotable in response to fluidic pressure variations applied on an upstream side thereof for achieving one way fluid flow through said passageway;
said flap means comprising a plurality of leaflet members that together in respective fully closed positions generally extend across said passageway in circumferentially adjacent, generally non-overlapping relationship, each said leaflet member including a peripheral portion that is curved circularly and also two peripheral portions that each extend radially; and a pair of opposed, flat outwardly extending ear members associated with each leaflet member, each one of said pair of ear members being located along a different opposite end area of said curved peripheral portion of said associated leaflet member, each ear member of said pair defining therebetween across their associated said leaflet member an eccentric pivot axis for said associated leaflet member, each said leaflet member being bent along said pivot axis and having a flat configuration on each side of said pivot axis;

said annular structure comprising a rigid ring member having in cross-section a C-type configuration with a mid-region and integral radially outturned longitudinally opposite ends and with a circumferentially extending inner face and a circumferentially extending outer face and also having defined in said mid-region at least two holes that radially extend through said ring member, each hole having sides that are radially inwardly tapered; at least two separate bearing housings, each one having at least one recess means defined in a circumferentially forward face thereof, having circumferentially extending groove means defined in a circumferentially rearward face thereof, and also having radially tapered side walls that are nestably and sealingly seated within a different one of said holes, there being one said recess means for pivotally journaling and holding each said ear member and also one said hole for each said bearing housing; and band means circumferentially and externally extending about said outer face in said mid-region for retaining said bearing housing in said holes; and the interrelationship between said flap means and said annular structure being such that each one of said leaflet members is independently pivotable between a fully open position and a fully closed position across said passageway with said ear members each being associated with a different one of said recess means such that, when each one of said leaflet members is in said open position, one said side thereof is parallel to said longitudinal axis while the other said side thereof is inclined towards said longitudinal axis and towards said fully closed position; and edge portions of said ear members and of said leaflet member adjacent thereto wipe adjacent facial surface portions of said recess means and of said bearing housings adjacent thereto during pivotal movements of said leaflet members.

16. The assembly of claim 15 wherein said plurality of leaflet members cooperate with each other and with said circular structure to seal said passageway when said leaflet members are in their respective closed positions.

17. The assembly of claim 15 wherein peripheral edge portions of said ear members and side wall portions of said recesses each have mating spherical curvatures.

18. The assembly of claim 15 wherein said recess side wall portions exist only in quadrants over which said ear member edge portions pass when said leaflet members move between their open and closed positions.

19. The assembly of claim 15 wherein each said forward face of each said bearing housing is flat and extends perpendicularly to said pivot axis of leaflet member one of whose said ear member is associated with said recess that is defined in each said forward face; and wherein each of said leaflet members is flattened in edge portions thereof adjacent to each ear member associated therewith so that said adjacent flattened edge portions wipe said flat forward facial portions when said leaflet members pivot.

20. The assembly of claim 15 wherein each said bearing housing has two circumferentially adjacent said recesses whose respective axes are perpendicular to each other, and each one of said recesses is coaxial with the pivot axis of said leaflet member, one of whose said ear members is associated with said one recess.

21. The assembly of claim 15 wherein circumferential channel means is defined in rearward facial portions of each said bearing housing and said band means extends in said channel means.

22. The assembly of claim 15 wherein each bearing housing includes stop means limiting radial movements of said bearing housings into said passageway through their respective associated said holes.

23. A prosthetic heart valve assembly comprising:
  (a) an annular structure having a central passageway; and
  (b) flap means disposed across said passageway and pivotable in response to fluidic pressure variations applied on an upstream side thereof for achieving one way fluid flow through said passageway;

said flap means comprising leaflet means that generally extends across said passageway; and flat outwardly extending ear members along outer peripheral portions of said leaflet means;

said annular structure comprising a rigid ring member having in cross-section a C-type configuration with a mid-region and integral radially outturned opposite ends and also having defined in said mid-region at least two circumferentially spaced holes that radially extend through said ring member, each said hole having sides that are radially inwardly tapered; at least two separate bearing housing each one have recess means defined in a forward face thereof and also having a tapered side wall that is nestably and sealingly seatable within a different one of said holes, there being one said recess means for pivotally receiving and holding each said ear member, and also one said hole for each said bearing housing; and band retaining means extending circumferentially completely around said outer face in said mid-region for holding said bearing housings in said holes;

and the interrelationship between said flap means and said annular structure being such that said leaflet means is pivotable between open and closed positions across said passageway with said ear members each being associated with a different one of said recess means; and edge portions of said ear members and of said leaflet means adjacent thereto wipe adjacent facial portions of said recesses and of said bearing housings adjacent thereto during pivotal movements of said leaflet member.

* * * * *